(12) United States Patent
Yoshida et al.

(10) Patent No.: US 9,056,096 B2
(45) Date of Patent: Jun. 16, 2015

(54) HYALURONIC ACID DECOMPOSITION-PROMOTING FACTOR AND INHIBITOR THEREOF

(75) Inventors: Hiroyuki Yoshida, Odawara (JP); Shintaro Inoue, Odawara (JP); Shingo Sakai, Odawara (JP); Aya Nagaoka, Odawara (JP)

(73) Assignee: Kao Corporation, Tokyo (JP)

( * ) Notice: Subject to any disclaimer, the term of this patent is extended or adjusted under 35 U.S.C. 154(b) by 123 days.

(21) Appl. No.: 13/701,702

(22) PCT Filed: Jun. 3, 2011

(86) PCT No.: PCT/JP2011/003158
§ 371 (c)(1),
(2), (4) Date: Dec. 3, 2012

(87) PCT Pub. No.: WO2011/152071
PCT Pub. Date: Dec. 8, 2011

(65) Prior Publication Data
US 2013/0095110 A1 Apr. 18, 2013

(30) Foreign Application Priority Data
Jun. 4, 2010 (JP) .................................. 2010-128701

(51) Int. Cl.
| | |
|---|---|
| G01N 33/53 | (2006.01) |
| A61K 39/395 | (2006.01) |
| A61K 8/42 | (2006.01) |
| A61K 8/44 | (2006.01) |
| A61K 8/49 | (2006.01) |
| A61K 31/365 | (2006.01) |
| A61K 31/4015 | (2006.01) |
| A61K 31/5415 | (2006.01) |
| A61K 31/7088 | (2006.01) |
| A61K 31/713 | (2006.01) |
| A61K 48/00 | (2006.01) |
| A61Q 19/08 | (2006.01) |
| C07K 14/47 | (2006.01) |
| C07K 16/40 | (2006.01) |
| C12N 15/113 | (2010.01) |
| G01N 33/50 | (2006.01) |
| A61K 31/16 | (2006.01) |
| A61K 31/198 | (2006.01) |
| A61K 31/7048 | (2006.01) |
| C07K 7/08 | (2006.01) |
| C07K 16/18 | (2006.01) |
| C12Q 1/02 | (2006.01) |
| A61K 8/64 | (2006.01) |
| A61K 8/73 | (2006.01) |
| A61K 31/728 | (2006.01) |
| A61K 38/00 | (2006.01) |

(52) U.S. Cl.
CPC .............. *A61K 39/3955* (2013.01); *A61K 8/42* (2013.01); *A61K 8/44* (2013.01); *A61K 8/49* (2013.01); *A61K 8/4913* (2013.01); *A61K 8/498* (2013.01); *A61K 31/365* (2013.01); *A61K 31/4015* (2013.01); *A61K 31/5415* (2013.01); *A61K 31/7088* (2013.01); *A61K 31/713* (2013.01); *A61K 38/00* (2013.01); *A61K 48/005* (2013.01); *A61K 2800/782* (2013.01); *A61Q 19/08* (2013.01); *C07K 14/47* (2013.01); *C07K 16/40* (2013.01); *C12N 15/113* (2013.01); *C12N 2310/14* (2013.01); *G01N 33/5023* (2013.01); *A61K 31/16* (2013.01); *A61K 31/198* (2013.01); *A61K 31/7048* (2013.01); *C07K 7/08* (2013.01); *C07K 16/18* (2013.01); *C12Q 1/025* (2013.01); *C07K 2317/34* (2013.01); *A61K 8/64* (2013.01); *A61K 8/735* (2013.01); *C12N 2310/11* (2013.01); *G01N 2500/10* (2013.01); *A61K 31/728* (2013.01); *G01N 2400/40* (2013.01)

(58) Field of Classification Search
None
See application file for complete search history.

(56) References Cited

U.S. PATENT DOCUMENTS

| | | |
|---|---|---|
| 2004/0209275 A1 | 10/2004 | Liew et al. |
| 2005/0025825 A1 | 2/2005 | Heasley et al. |
| 2006/0127476 A1 | 6/2006 | Heasley et al. |
| 2009/0017114 A1 | 1/2009 | Heasley et al. |
| 2009/0048115 A1 | 2/2009 | Liew et al. |

(Continued)

FOREIGN PATENT DOCUMENTS

| | | |
|---|---|---|
| DE | 103 28 033 A1 | 1/2005 |
| EP | 1 553 101 A1 | 7/2005 |

(Continued)

OTHER PUBLICATIONS

Extended European search report for EP Appl. No. 11789484.0, including the supplementary European search report and the European search opinion, mailed Oct. 22, 2013, European Patent Office, Rijswijk, Netherlands.

Allison DD et al., "Review. Hyaluronan: a powerful tissue engineering tool," Tissue Eng 12(8): 2131-2140, (Aug. 2006), Mary Ann Liebert, Inc., New Rochelle, NY.

(Continued)

*Primary Examiner* — Maher Haddad
(74) *Attorney, Agent, or Firm* — Sterne, Kessler, Goldstein & Fox P.L.L.C.

(57) ABSTRACT

The present invention is directed to KIAA1199, which is a novel factor involved in decomposition of hyaluronic acid, and to use thereof. More specifically, the invention is directed to a hyaluronic acid decomposition-promoting agent containing the KIAA1199 gene and a protein encoded by the gene; to a hyaluronic acid decomposition-inhibiting agent characterized by inhibiting the activity or expression thereof (including an siRNA or a monoclonal antibody); and to a method for screening a novel hyaluronic acid decomposition-controlling agent, in which the method contains employing the expression of KIAA1199 as an index.

4 Claims, 15 Drawing Sheets

(56) References Cited

U.S. PATENT DOCUMENTS

| | | | |
|---|---|---|---|
| 2009/0163434 | A1 | 6/2009 | Bader et al. |
| 2009/0208514 | A1 | 8/2009 | Nakamura et al. |
| 2009/0214644 | A1 | 8/2009 | Heasley et al. |
| 2011/0201669 | A1 | 8/2011 | Cao |
| 2012/0021946 | A1 | 1/2012 | Nakamura et al. |

FOREIGN PATENT DOCUMENTS

| | | | |
|---|---|---|---|
| JP | 08-157321 A | 6/1996 | |
| JP | 08-225447 A | 9/1996 | |
| JP | 11-080004 A | 3/1999 | |
| JP | 11-080205 A | 3/1999 | |
| JP | 11-279205 A | 10/1999 | |
| JP | 2006-076975 A | 3/2006 | |
| JP | 2008-118915 A | 5/2008 | |
| JP | 2009-502116 A | 1/2009 | |
| JP | 2009-276153 A | 11/2009 | |
| WO | WO 02/13796 A2 | 2/2002 | |
| WO | WO 2004/024892 A2 | 3/2004 | |
| WO | WO 2005/011650 A1 | 2/2005 | |
| WO | WO 2010/011281 A2 | 1/2010 | |

OTHER PUBLICATIONS

Harada H et al., "CD44-dependent Intracellular and Extracellular Catabolism of Hyaluronic Acid by Hyaluronidase-1 and -2," J. Biol. Chem. 282: 5597-5607, (Feb. 2007), Am Soc Biochem Mol Biol, Baltimore, MD.

International Search Report (ISR) for PCT/JP2011/003158, I.A. fd: Jun. 3, 2011, mailed Aug. 30, 2011 from the Japanese Patent Office, Tokyo, Japan.

International Preliminary Report on Patentability (IPRP), Chapter I of the Patent Cooperation Treaty, including the Written Opinion for PCT/JP2011/003158, I.A. fd: Jun. 3, 2011, issued Jan. 8, 2013, from the International Bureau of WIPO, Geneva, Switzerland.

Abe, S. et al., "Indentification of *CRYM* as a candidate responsible for nonsyndromic deafness, through cDNA microarray analysis of human cochlear and vestibular tissues," Am J Hum Genet, Jan. 2003; 72(1): 73-82, University of Chicago Press, Chicago, IL.

Abe, S et al., "Mutations in the gene encoding KIAA1199 protein, an inner-ear protein expressed in Deiters' cells and the fibrocytes, as the cause of nonsyndromic hearing loss," J Hum Genet, Jan. 2003; 48(11): 564-570, University of Chicago Press, Chicago, IL.

Michishita, E et al., "Upregulation of the KIAA1199 gene is associated with cellular mortality," Cancer Lett, Jul. 2006; 239(1): 71-77, Elsevier Science Ireland, Limerick, Ireland.

Sabates-Bellver, J et al., "Transcriptome Profile of Human Colorectal Adenomas," Mol. Cancer Res., Dec. 2007; 5: 1263-1275, Amer. Assoc. for Cancer Research, Philadelphia, PA.

Galamb, O et al., "Reversal of gene expression changes in the colorectal normal-adenoma pathway by NS398 selective COX2 inhibitor," Br J Cancer, Feb. 2010; 102(4): 765-773, Nature Publishing Group on behalf of Cancer Research UK, London, UK.

Extended European search report for EP Appl. No. 14179168.1.0, including the supplementary European search report and the European search opinion, mailed Dec. 16, 2014, European Patent Office, Rijswijk, Netherlands.

Usami, S et al., "The localization of proteins encoded by CRYM, KIAA1199, UBA52, COL9A3, and COL9A1, genes highly expressed in the cochlea," Neuroscience, Jun. 2008; 154(1): 22-28, Elsevier, New York.

Dias Neto, E et al., "Shotgun sequencing of the human transcriptome with ORF expressed sequence tags," Proc Natl Acad Sci (USA), Mar. 2000; 97: 3491-3496, National Academy of Sciences, Washington, DC.

Arao, T et al., "KIAA1199 is a novel therapeutic target for gastic cancer," AACR Meeting Abstracts Online, 98th AACR Annual Meeting, Apr. 14-18, 2007, Los Angeles, CA, Abstract No. 1987, American Association for Cancer Research, Philadelphia, PA, retrieved from the Internet on Dec. 1, 2014: http://aacrmeetingabstracts.org/cgi/content/short/2007/1__Annual__Meeting/1987.

Birkenkamp-Demtroder, K et al., "Repression of KIAA1199 attenuates Wnt-signalling and decreases the proliferation of colon cancer cells," Br J Cancer, Aug. 2011; 105(4): 552-561, Nature Publishing Group on behalf of Cancer Research UK, London, UK.

HYALURONIC ACID DECOMPOSITION-PROMOTING FACTOR AND INHIBITOR THEREOF

FIELD OF THE INVENTION

The present invention relates to a novel hyaluronic acid decomposition-promoting factor and to an inhibitor thereof. More particularly, the invention relates to a hyaluronic acid decomposition-promoting agent containing a KIAA1199 gene and a protein encoded by the gene, to a hyaluronic acid decomposition-inhibiting agent which can inhibit activity or expression of the gene and inhibit activity or expression of the protein, and the like.

BACKGROUND OF THE INVENTION

Hyaluronic acid is a type of muco-polysaccharide which is present at high level in the dermis and which maintains moisture and elasticity of the skin. The half-life of hyaluronic acid is as short as about one day, and hyaluronic acid level is known to decrease with aging. Thus, hitherto, hyaluronic acid and substances which can suppress decomposition of hyaluronic acid have been employed as, for example, cosmetics for the moisturizing or anti-aging purpose.

For example, some plant extracts, histamine H1-antagonist (Patent Document 1), and heparin (Patent Document 2) are known to have a hyaluronic acid decomposition-suppressing effect, and application of these substances to cosmetics and pharmaceuticals is now studied. Meanwhile, a chondroitin sulfate C derivative (Patent Document 3) and carnitine derivatives (Patent Document 4) are known to have a hyaluronic acid decomposition promoting effect.

In the beauty and medical fields, local injection of hyaluronic acid is widely known to provide a wrinkle-ameliorating effect. However, since the injected hyaluronic acid is decomposed and metabolized by an enzyme present in the body, the effect thereof cannot last for a long period, which is problematic.

In the pharmaceutical field, an intra-articular injection of high-molecule hyaluronic acid is used for the treatment of deformans arthritis or rheumatoid arthritis. However, due to a poor long-lasting effect, patients must periodically receive the injection. Thus, if decomposition of hyaluronic acid in the body can be controlled, the aforementioned poor long-lasting effect can be solved, whereby patient's compliance would be improved.

Hyaluronic acid is a polymer having a repeated structure formed of D-glucuronic acid and N-acetyl-D-glucosamine, and the molecular weight thereof ranges from the order of 1,000 to the order of 1,000,000. The physiological activity of hyaluronic acid is known to vary depending on its molecular weight. For example, a low-molecule hyaluronic acid having a molecular weight of 1,600 to 10,000 is known to exhibit angiogenesis action, while hyaluronic acid having a molecular weight of about 500,000 or less is known to induce various inflammation-related factors.

In diseases such as cancer, deformans arthritis (OA), and rheumatoid arthritis (RA), the synthesis/decomposition balance of hyaluronic acid is known to be lost. In bladder cancer, a large amount of low-molecule hyaluronic acid is detected in urine and bladder tissue. The malignancy of the cancer is correlated to the molecular weight of hyaluronic acid in the relevant tissue. In the case of high-malignancy cancer, both hyaluronic acid having a high molecular weight (about 2,000,000) and hyaluronic acid having a low molecular weight (about 10,000) are present. According to one report, low-molecule hyaluronic acid induces genesis of feeding vessels to the tumor tissue. The level and molecular weight of hyaluronic acid are known to decrease in the joint fluid of deformans arthritis patients and rheumatoid arthritis patients. Therefore, if the molecular weight of hyaluronic acid can be controlled, the desired effect of hyaluronic acid depending on the molecular weight can be attained, possibly leading to more effective therapy.

Meanwhile, there has been proposed a model of decomposition/metabolism of hyaluronic acid in the body which involves hyaluronidase (HYAL)1, HYAL2, and CD44 (HA receptor). According to the model, hyaluronic acid is decomposed outside the cells by the cooperative action of HYAL2 and CD44, to thereby form a 20 kDa fragment, or is incorporated into the endosome/lysosome path by the mediation of CD44, and decomposed by HYAL1 in lysosome to tetrasaccharide.

At present, six human hyaluronidase-related genes (HYAL1 to HYAL4, SPAM1, and HYALP1) are known. Proteins encoded by HYAL4, SPAM1, and HYALP1 are produced mainly in the testicles, while proteins encoded by HYAL1, HYAL2, and HYAL3 are present widely in the body. At present, the hyaluronic acid decomposition action of HYAL3 has not been clearly elucidated, and therefore, the aforementioned HYAL1 and HYAL2 are thought to have a high possibility of playing a main role in decomposition of hyaluronic acid. However, the mechanism of decomposition of hyaluronic acid cannot be completely elucidated only from the known hyaluronidase-related genes, and the actual mechanism is currently unknown.

The KIAA1199 gene of the present invention is a function-unknown expressed sequence tag (EST), and the KIAA1199 gene was suggested to have a relationship with cancer or hearing impairment. For example, the KIAA1199 gene is highly expressed in the inner ear, and a plurality of cases of mutation in the KIAA1199 gene involving amino acid substitution were found in family lineages having nonsyndromic hearing impairment (see, for example, Non-Patent Documents 1 and 2). Also, in a variety of cancer cells and cancer tissues such as cultured breast cancer cells and stomach cancer, the KIAA1199 gene is highly expressed (see Non-Patent Documents 3 and 4). The KIAA1199 gene is highly expressed in colorectal cancer, and the level is reduced through administration of an anti-cancer agent (see Non-Patent Document 5). On the basis of the aforementioned findings and use of the KIAA1199 gene for cancer genetic diagnosis and drug development, some patent applications were filed (Patent Documents 5 to 9).

Meanwhile, some analyses by means of a microarray have revealed that the KIAA1199 gene may serve as a marker for deformans arthritis (Patent Document 10) and rheumatoid arthritis and osteoarthritis (Patent Document 11).

However, due to complex mechanisms in relation to cancer and inflammation, no specific physiological functions of the KIAA1199, including physiological activities and involvement in cancer and inflammation, have been clearly elucidated.

PRIOR ART DOCUMENTS

Patent Documents

Patent Document 1: JP-A-1996-225447
Patent Document 2: JP-A-1999-80004
Patent Document 3: JP-A-1999-80205
Patent Document 4: JP-A-2006-76975
Patent Document 5: WO2005/011650

Patent Document 6: JP-A-2008-118915
Patent Document 7: JP-A-2009-276153
Patent Document 8: Japanese Kohyo (PCT) Patent Publication No. 2009-502116
Patent Document 9: WO2010/011281
Patent Document 10: Japanese Kohyo (PCT) Patent Publication No. 2006-506979
Patent Document 11: DE10328033

Non-Patent Documents

Non-Patent Document 1: Abe S, et al., Am. J. Hum. Genet. 72(1): 73-82 (2003)
Non-Patent Document 2: Abe S, et al., J. Hum. Genet. 48(11): 564-570 (2003)
Non-Patent Document 3: Michishita E, et al., Cancer Lett. 239: 71-77 (2006)
Non-Patent Document 4: Sabates-Bellver J, et al., Mol. Cancer. Res. 12: 1263-75 (2007)
Non-Patent Document 5: Galamb O, et al., Br. J. Cancer 102 (4): 765-773 (2010)

SUMMARY OF THE INVENTION

Problems to be Solved by the Invention

The present invention relates to finding a factor relating to decomposition of hyaluronic acid, and providing novel means for the treatment of a disease caused by hyaluronic acid or decomposition or metabolism of hyaluronic acid by controlling the activity and expression of the factor.

Means for Solving the Problems

The present inventors have found a hyaluronic acid decomposition factor other than HYAL1, HYAL2, and CD44 in human fibroblasts, and have identified, through knocking down candidate genes of the factor, a gene represented by a gene symbol of KIAA1199 (i.e., KIAA1199 gene) as the factor. Thus, the inventors have found that KIAA1199 is the novel factor involved in decomposition of hyaluronic acid.

The KIAA1199 gene is a function-unknown expressed sequence tag (EST). As described above, the KIAA1199 gene was suggested to have a relationship with cancer or hearing impairment, but no report has been published on the relationship between the KIAA1199 gene and hyaluronic acid or the decomposition and metabolism of hyaluronic acid. The present inventors have elucidated the mechanism of KIAA1199-mediated decomposition of hyaluronic acid by use of siRNA or a monoclonal antibody to the KIAA1199 gene, and have found that decomposition of hyaluronic acid can be effectively suppressed by inhibiting expression and activity of KIAA1199.

Accordingly, the present invention relates to a hyaluronic acid decomposition-promoting function of KIAA1199 and inhibition thereof.

In a first embodiment of the present invention, there is provided a method for selecting, through screening, a hyaluronic acid decomposition-controlling agent.

In one embodiment of the screening method, the hyaluronic acid decomposition controlling effect of a test substance is assessed on the basis of the expression level of the KIAA1199 gene or the protein encoded by the KIAA1199 gene as an index.

The screening method contains, for example, the following steps:
1) culturing cells in the presence or absence of a test substance;
2) determining the expression level of the KIAA1199 gene or a protein encoded by the KIAA1199 gene in the cells; and
3) assessing the hyaluronic acid decomposition controlling effect of the test substance on the basis of the difference between the expression level of the KIAA1199 gene or the protein encoded by the KIAA1199 gene in the cells determined in the presence of the test substance and that determined in the absence of the test substance.

In the above method, cells in which the KIAA1199 gene is highly expressed transiently or stably are preferably employed. The cells may be recombinant cells that have been forced to express the KIAA1199 gene.

In another embodiment of the screening method, the hyaluronic acid decomposition controlling effect of a test substance is assessed on the basis of, as an index, the molecular weight of labeled hyaluronic acid added to the test substance exogenously.

The screening method contains, for example, the following steps:
1) culturing cells in which the KIAA1199 gene is highly expressed transiently or stably in coexistence with a labeled hyaluronic acid in the presence or absence of a test substance;
2) recovering the culture supernatant after culturing, and determining the molecular weight of the labeled hyaluronic acid; and
3) assessing the hyaluronic acid decomposition controlling effect of the test substance on the basis of the difference between the molecular weight of the labeled hyaluronic acid determined in the presence of the test substance and that determined in the absence of the test substance.

In a second mode of the present invention, there is provided a method for controlling decomposition of hyaluronic acid, characterized by including controlling the expression or activity of the KIAA1199 gene or a protein encoded by the KIAA1199 gene.

In the case where decomposition of hyaluronic acid is inhibited, the above method contains, for example, a step of applying (e.g., administering, incorporating), to a subject in need thereof,
i) an anti-sense nucleic acid or an siRNA against the KIAA1199 gene,
ii) an antibody specific to the protein encoded by the KIAA1199 gene, or
iii) a low-molecule compound selected from the group consisting of chlorpromazine, N-ethylmaleimide, bafilomycin A1, monensin, EDTA, deferoxamine, and orientin.

In the case where decomposition of hyaluronic acid is promoted, the above method contains, for example, a step of applying (e.g., administering, incorporating), to a subject in need thereof,
i) the KIAA1199 gene,
ii) the protein encoded by the KIAA1199 gene, or
iii) a substance which can promote the expression or activity of the KIAA1199 gene or the protein encoded by the KIAA1199 gene.

In a third embodiment of the present invention, there is provided a hyaluronic acid decomposition-controlling agent containing a substance which can control the expression or activity of the KIAA1199 gene or the protein encoded by the KIAA1199 gene.

In the case where decomposition of hyaluronic acid is inhibited, the hyaluronic acid decomposition-controlling agent; i.e., the hyaluronic acid decomposition-inhibiting agent, of the present invention, contains, for example, i) an anti-sense nucleic acid or an siRNA against the KIAA1199 gene, ii) an antibody specific to the protein encoded by the KIAA1199 gene, or iii) a low-molecule compound selected from the group consisting of chlorpromazine, N-ethylmaleimide, bafilomycin A1, monensin, EDTA, deferoxamine, and orientin.

The aforementioned siRNA has a nucleotide sequence represented by any of SEQ ID NOs: 6 to 8 in the sequence list, or a nucleotide sequence having an identity of 900 or higher with respect thereto.

Examples of the aforementioned antibody include an antibody which is specific to a peptide having an amino acid sequence represented by any of SEQ ID NOs: 3 to 5 in the sequence list, and an antibody which is specific to a peptide having an amino acid sequence having an identity of 90% or higher with respect thereto.

Examples of the aforementioned low-molecule compound include chlorpromazine, N-ethylmaleimide, bafilomycin A1, monensin, EDTA, deferoxamine, and orientin.

The aforementioned hyaluronic acid decomposition-inhibiting agent may serve as a pharmaceutical composition or a cosmetic composition.

The hyaluronic acid decomposition-inhibiting agent of the present invention may be employed for the prevention, treatment, or amelioration of a condition or a disease accompanying anomalous decomposition of hyaluronic acid. Specifically, the agent is employed for, for example, improvement of joint functions, prevention and treatment of cancer, restoration of tissue, amelioration of skin roughness or dry skin, or reduction of wrinkles.

In the case where decomposition of hyaluronic acid is promoted, the hyaluronic acid decomposition-controlling agent; i.e., the hyaluronic acid decomposition-promoting agent, contains, for example, i) the KIAA1199 gene, ii) the protein encoded by the KIAA1199 gene, or iii) a substance which can promote the expression or activity of the KIAA1199 gene or the protein encoded by the KIAA1199 gene.

The aforementioned hyaluronic acid decomposition-promoting agent may serve as a pharmaceutical composition or a cosmetic composition.

The hyaluronic acid decomposition-promoting agent of the present invention is employed for the prevention, treatment, or amelioration of a condition or a disease accompanying anomalous production promotion or anomalous decomposition suppression of hyaluronic acid, modulation of tissue restoration by hyaluronic acid, or the prevention or treatment of hearing impairment.

The present invention also provides a topical preparation containing hyaluronic acid or a pharmacologically acceptable salt or derivative thereof, and the aforementioned hyaluronic acid decomposition-inhibiting agent. The topical preparation may serve as a joint function-improving agent, a tissue-restoring agent, or a cosmetic composition.

The present invention also provides a kit for assessing the hyaluronic acid decomposition controlling effect of the present invention (i.e., a hyaluronic acid decomposition controlling effect assessing kit). The kit contains at least one of the following (a) to (d):

(a) cells in which the KIAA1199 gene is highly expressed transiently or stably;

(b) a monoclonal antibody specific to the protein encoded by the KIAA1199 gene;

(c) an oligonucleotide primer for specifically amplifying the KIAA1199 gene; and (d) a polynucleotide probe for detecting the KIAA1199 gene by binding specifically to the gene.

Examples of the aforementioned antibody include an antibody which is specific to a peptide having an amino acid sequence represented by any of SEQ ID NOs: 3 to 5 in the sequence list, and an antibody which is specific to a peptide having an amino acid sequence having an identity of 90% or higher with respect thereto.

The present invention also provides the aforementioned monoclonal antibody and an epitope peptide thereof. The epitope peptide has an amino acid sequence represented by any of SEQ ID NOs: 3 to 5 in the sequence list, or an amino acid sequence having an identity of 90% or higher with respect thereto.

Effects of the Invention

According to the present invention, through controlling decomposition of hyaluronic acid in the body, diseases and conditions, which would otherwise be caused by exhaustion or reduction in molecular weight of hyaluronic acid, can be mitigated or cured. Also, the effect of locally injected hyaluronic acid can be maintained in the treatment of osteoarthritis or rheumatoid arthritis and in the beauty and medical fields. Furthermore, through employment of the KIAA1199 gene or a protein encoded by the KIAA1199 gene as a target, a novel hyaluronic acid decomposition-controlling agent can be retrieved, and the mechanism of a pathological condition caused by decomposition of hyaluronic acid can be elucidated.

Figure 1A:
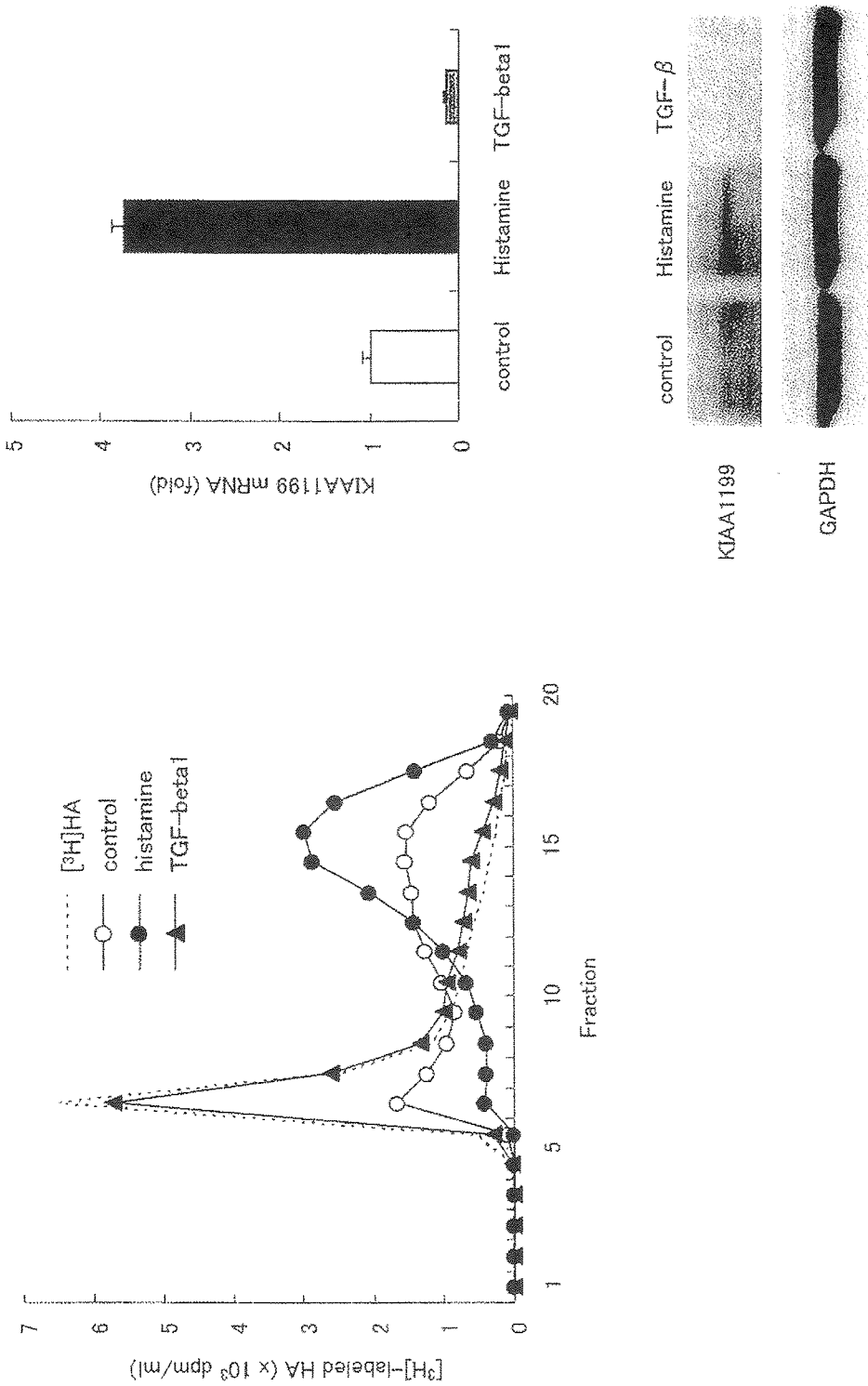
FIG. 1a Decomposition of HA by histamine or TGF-β1 in cultured normal human skin fibroblasts (Detroit551) (left); detection of expression of KIAA1199 mRNA through RT-PCR (right, top), and detection of expression of KIAA1199 protein through western blotting (right, bottom).

The present specification contains the content of the entirety of the specification of Japanese Patent Application No. 2010-128701, which is a basic application to which the present application claims priority.

MODES FOR CARRYING OUT THE INVENTION

The present invention is directed to application of the hyaluronic acid decomposition-promoting function of a gene represented by a gene symbol of KIAA1199 (hereinafter referred to as a "KIAA1199 gene") or a protein encoded by the KIAA1199 gene (hereinafter referred to as a "KIAA protein") to therapy, diagnosis, and drug development.

Hereinafter, the present invention will be described in detail.

1. KIAA1199

The "KIAA1199 gene" of the present invention is a function-unknown expressed sequence tag (EST) represented by a gene symbol of KIAA1199 and may also be represented by TMEM2L.

The nucleotide sequence and amino acid sequence (ORF) of the human KIAA1199 are known. The nucleotide sequence (mRNA) and the amino acid sequence are registered with an Accession Number NM_018689 and Accession Number EAW99111 in a public database, GenBank.

In the sequence list attached to the specification, the nucleotide sequence of the human KIAA1199 is represented by SEQ ID NO: 1, and the amino acid sequence thereof is represented by SEQ ID NO: 2. In the present invention, the positions of the KIAA1199 gene, and the positions of the amino acid sequence of the KIAA1199 protein are specified by the positions shown in SEQ ID NO: 1 or 2.

The human KIAA1199 gene is located in the 15th chromosome, and the mRNA thereof consists of 7,080 nucleotides and codes for 1,361 amino acids (see SEQ ID NOs: 1 and 2).

The sequence of the KIAA1199 gene is known to be maintained widely in human, chimpanzee, dog, cow, mouse, rat, chicken, and zebrafish.

The "KIAA1199 protein" of the present invention is a protein encoded by the KIAA1199 gene. The human KIAA1199 protein (ORF) consists of 1,361 amino acids and is reported to have GG domain (i.e., a sequence of about 100 amino acids consisting of 7 β-strands and 2 α-helixes, defining no function) and G8 domain (i.e., an amino acid sequence consisting of 5 β-strands, defining no function), elucidated through computer analysis.

Some studies have revealed that the KIAA1199 gene, which is highly expressed in a certain cancer patients, can be employed as a marker for the diagnosis of such cancer. Also, since cases of mutation in the KIAA1199 gene involving amino acid substitution were found in family lineages having nonsyndromic hearing impairment, the relationship between the KIAA1199 gene and hearing impairment has been suggested. However, functions of KIAA1199 in the body have not been clearly elucidated, and the treatment of diseases by use of the KIAA1199 gene or KIAA1199 protein has not been reported.

The present inventors have first found that KIAA1199 serves as a hyaluronic acid decomposition-promoting factor in a hyaluronic acid decomposition system which is different from a known hyaluronic acid decomposition system by the mediation of HYAL1, HYAL2, or CD44.

The present inventors have also confirmed the following phenomena. In a study on normal synovial cells and cultured synovial cells of osteoarthritis (OA) patients and rheumatoid arthritis (RA) patients, who are known to have a hyaluronic acid metabolism disorder, the KIAA1199 gene expression level increases in the order of normal, OA, and RA, and decomposition of hyaluronic acid is promoted in the order of normal, OA, and RA. When the KIAA1199 gene was knocked down in the above cells, decomposition of hyaluronic acid was suppressed in all types of the cells. In addition, in cultured synovial cells derived from an RA patient, expression of KIAA1199 was induced though addition of an inflammation-related mediator such as prostaglandin E2, IL-1, or IL-6. The above-confirmed phenomena support that KIAA1199 is a factor for promoting decomposition (excessive decomposition) of hyaluronic acid in a disease and that suppression of the function of KIAA1199 is useful for the treatment of diseases such as OA and RA, which would otherwise be caused by decomposition of hyaluronic acid.

2. Anti-Sense Nucleic Acid or siRNA for Suppressing Expression of the KIAA1199 Gene Anti-Sense Nucleic Acid The term "anti-sense nucleic acid" refers to a nucleic acid having a nucleotide sequence which is complementary or substantially complementary to a target nucleic acid or having a part of the nucleotide sequence. The anti-sense nucleic acid hybridizes with at least a portion of mRNA of the target nucleic acid (i.e., target site), to thereby suppress expression of the target nucleic acid. As used herein, the expression "substantially complementary" refers to allowance to include a partial mismatch, so long as the anti-sense nucleic acid hybridizes with the target site, to thereby suppress the target nucleic acid. Specifically, the "sequence substantially complementary to" the nucleotide sequence of the target site refers to a sequence complementary by 70% or higher, preferably 80% or higher, more preferably 90% or higher, even more preferably 95% or higher, to the nucleotide sequence of the target site.

A part of the nucleotides forming the anti-sense nucleic acid may be optionally modified so as to enhance stability in the body. Examples of such modification include phosphorothioation, methylphosphonation, and phosphorodithionation of a phosphate group; 2'-O-methylation of sugar (deoxyribose); chemical modification of a base; and incorporation of cross-linking (BNA (LNA) oligo). The nucleic acid may be DNA, RNA, or a hybrid thereof (DNA/RNA).

The target site of the "anti-sense nucleic acid" may be selected through a known method or an empirical rule. Examples of the method employed in the selection include a method in which a translation initiation site is selected; a method in which a site having a single strand structure is selected as a target site, the site being determined through calculation and prediction of the secondary structure from the primary structure; and a random screening method in which hybridization is performed at the highest efficiency by use of random oligo, to thereby select a cleavage site.

No particular limitation is imposed on the length of the anti-sense nucleic acid, so long as the purpose thereof can be attained. The length is generally 10 to 40 nucleotides, preferably 15 to 30 nucleotides.

siRNA (Small Interfering RNA)

The "siRNA (small interfering RNA)" is a small RNA molecule which suppresses expression of a target nucleic acid through RNA interference (i.e., decomposition of complementary mRNA), when double-strand RNA (dsRNA) is incorporated into cells.

The "siRNA" is designed as a short double-strand RNA (or RNA/DNA) of generally about 21 to about 30 nucleotides having an overhang (about 2 nucleotides) at an end, typically about 21 to about 25 nucleotides. The overhang site is generally designed as TT, but the design is not limited thereto. The siRNA may have a blunt end.

Similar to the case of the anti-sense nucleic acid, a part of the nucleotides forming an siRNA may be optionally modified so as to enhance stability in the body. Examples of such modification include phosphorothioation, methylphosphonation, and phosphorodithionation of a phosphate group; 2'-O-methylation of sugar (deoxyribose); chemical modification of a base; and incorporation of cross-linking (BNA (LNA) oligo). The nucleic acid is RNA, but may also be a hybrid thereof (DNA/RNA).

Similar to the case of the anti-sense nucleic acid, the target site of an siRNA may be selected through a known method or an empirical rule. In the selection, commercial software or a commercial service may be employed.

Accordingly, the "siRNA for suppressing the expression of the KIAA1199 gene" of the present invention is designed as a short double-strand RNA or RNA/DNA hybrid of about 21 to about 30 nucleotides, preferably about 21 to about 25 nucleotides, having a sequence complementary or substantially complementary to at least a part of the target domain predetermined through the above procedure.

For example, the siRNA of the present invention has a nucleotide sequence represented by any of SEQ ID NOs: 6 to 8 in the sequence list. However, the sequence is not limited thereto, and a similar siRNA having one or several (e.g., 1 to 3) mismatches, preferably about 1 or 2 mismatches, may also be used as the siRNA of the present invention, so long as the expression of the KIAA1199 gene can be suppressed. In other words, a siRNA having a sequence identity of 80% or higher, preferably 90% or higher, more preferably 95% or higher, with respect to a nucleotide sequence represented by any of SEQ ID NOs: 6 to 8, may also be used as the siRNA of the present invention, so long as the expression of the KIAA1199 gene can be suppressed.

The aforementioned anti-sense nucleic acid or siRNA may have an affinity to cell membrane enhanced through addition of PEG or polylysine thereto, or may be incorporated into a known controlled-release system employing liposome, microsphere, etc. The thus-formulated anti-sense nucleic acid or siRNA for suppressing the expression of the KIAA1199 gene is suitably used as the below-mentioned "hyaluronic acid decomposition-inhibiting agent."

3. Anti-KIAA1199 Antibody

The "antibody specific to a protein encoded by the KIAA1199 gene (anti-KIAA1199 antibody)" employed in the present invention may be prepared through a known method. Specifically, the antibody may be prepared through a routine method in which an animal is immunized by use of KIAA1199 protein serving as an antigen or any partial polypeptide thereof, and the antibody produced in the animal is recovered and purified.

The antibody may be a polyclonal antibody, but a monoclonal antibody is preferred. The monoclonal antibody may be prepared through a known method (e.g., Kohler and Milstein, Nature 256, 495 to 497, 1975, Kennet, R. ed., Monoclonal Antibody p. 365 to 367, 1980, Prenum Press, N.Y.) in which a hybridoma is established through fusion of antibody-producing cells which produce a specific antibody, and myeloma cells.

Examples of the antigen for producing the antibody include KIAA1199 protein (antigen), a partial polypeptide consisting of a continuous amino acid partial sequence thereof (epitope peptide), or a derivative thereof to which any of the amino acid sequences or a carrier (e.g., N-terminal-adding keyhole limpet hemocyanine) has been added.

The antigen polypeptide may be prepared by producing KIAA1199 protein or a partial polypeptide (epitope peptide) in host cells through genetic technique. Specifically, a vector which can express the KIAA1199 gene or a part thereof is produced, and the vector is incorporated into the host cells, to thereby express the gene.

For example, the anti-KIAA1199 antibody may be produced such that a peptide having an amino acid sequence represented by any of SEQ ID NOs: 3 to 5 in the list serves as an epitope. However, the sequence is not limited thereto, and a antibody which is produced such that a peptide having an amino acid sequence in which one or several amino acids are deleted, substituted, or added serves as an epitope, may also be used as the anti-KIAA1199 (monoclonal) antibody of the present invention, so long as the antibody can bind specifically to KIAA1199 protein, to thereby suppress the function of KIAA1199. In other words, an antibody which is produced such that a peptide having an amino acid sequence with an identity of 80% or higher, preferably 90% or higher, more preferably 95% or higher, with respect to the amino acid sequence represented by any of SEQ ID NOs: 3 to 5 in the list serves as an epitope may also be used as the anti-KIAA1199 (monoclonal) antibody of the present invention, so long as the antibody can bind specifically to KIAA1199 protein, to thereby suppress the function of KIAA1199.

The anti-KIAA1199 antibody may be labeled in accordance with needs. No particular limitation is imposed on the label, but the label is preferably an enzyme (alkaline phosphatase or horse radish peroxidase) or biotin (operation in which enzyme labeled streptavidin is bound to biotin serving as a secondary antibody, is added).

The thus-formulated antibody, particularly a high-specificity monoclonal antibody, may be suitably employed as the below-mentioned "hyaluronic acid decomposition-inhibiting agent."

KIAA1199 Epitope Peptide

The present inventors have confirmed that a monoclonal antibody having an amino acid sequence represented by any of SEQ ID NOs: 3 to 5 in the sequence list serving as an epitope exhibits high specificity and excellent KIAA1199 suppression effect. Thus, the present invention also provides a "KIAA1199 epitope peptide" represented by any of SEQ ID NOs: 3 to 5.

So long as the epitope peptide serves as an anti-KIAA1199 antibody epitope, the epitope peptide may be a peptide which has an amino acid sequence in which one or several amino acids are deleted, substituted, or added in the amino acid sequence represented by any of SEQ ID NOs: 3 to 5. In other words, a peptide having an amino acid sequence with an identity of 80% or higher, preferably 90% or higher, more preferably 95% or higher, with respect to the amino acid sequence represented by any of SEQ ID NOs: 3 to 5 may also be employed as the "KIAA1199 epitope peptide" of the present invention.

4. Hyaluronic Acid Decomposition-Controlling Agent

The "hyaluronic acid decomposition-controlling agent" of the present invention is a substance or preparation which controls the expression or activity of the KIAA1199 gene or KIAA1199 protein, whereby decomposition of hyaluronic acid via KIAA1199 is controlled (inhibited or promoted). That is, the "hyaluronic acid decomposition-controlling agent" of the present invention encompasses both the "hyaluronic acid decomposition-inhibiting agent" and the "hyaluronic acid decomposition-promoting agent" described hereinbelow.

4.1 Hyaluronic Acid Decomposition-Inhibiting Agent

The "hyaluronic acid decomposition-inhibiting agent" of the present invention is a substance or preparation which suppresses the expression or activity of the KIAA1199 gene or KIAA1199 protein, whereby decomposition of hyaluronic acid via KIAA1199 is inhibited.

As described above, the anti-sense nucleic acid or siRNA to the KIAA1199 gene serves as the "hyaluronic acid decomposition-inhibiting agent" by suppressing the expression of the KIAA1199 gene. The anti-KIAA1199 antibody, particularly a high-specificity monoclonal antibody, serves as the "hyaluronic acid decomposition-inhibiting agent" by specifically inhibiting the activity of the KIAA1199 protein. Furthermore, low-molecule compounds such as chlorpromazine, N-ethylmaleimide, bafilomycin A1, monensin, EDTA, deferoxamine, and orientin serve as the "hyaluronic acid decomposition-inhibiting agent" by inhibiting decomposition of hyaluronic acid via KIAA1199.

The "hyaluronic acid decomposition-inhibiting agent" of the present invention may contains any one of the anti-sense nucleic acid, siRNA, anti-KIAA1199 antibody, and one of the aforementioned low-molecule compounds, or may contain two or more members thereof.

If needed, the aforementioned anti-sense nucleic acid, siRNA, anti-KIAA1199 antibody, and low-molecule compounds are formulated with a pharmacologically acceptable carrier or additive. Formulation may be performed through a routine method (see, for example, Remington's Pharmaceutical Science, latest edition, Mark Publishing Company, Easton, U.S.A).

Examples of the pharmacologically acceptable carrier or additive include a surfactant, a vehicle, a colorant, a flavoring agent, a preservative, a stabilizer, a buffer, a suspending agent, a tonicity agent, a binder, a disintegrant, a lubricant, a fluidity-prompter, and a corrigent. Specific examples of the carrier which may be employed in the invention include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium-chain fatty acid triglyceride, polyoxyethylene-hydrogenated castor oil 60, succharose, carboxymethylcellulose, corn starch, and inorganic salts.

The "hyaluronic acid decomposition-inhibiting agent" of the present invention may be administered perorally or parenterally, but parenteral administration is preferred. Examples of the administration method include injection, transnasal administration, transpulmonary administration, and percutaneous administration. Examples of the injection include intravenous injection, intramuscular injection, intraperitoneal injection, and subcutaneous injection. The administration method may be appropriately selected in accordance with the age and symptoms of a patient, and may be systemic or topic. Topical administration is preferred.

No particular limitation is imposed on the dose of the agent, and the unit dose is appropriately selected within, for example, a range of 0.0001 mg/kg to 1,000 mg/kg. Alternatively, the dose for one patient is appropriately selected within a range of 0.001 to 100,000 mg/body. Prevention, treatment, and amelioration of conditions or diseases accompanying anomalous decomposition of hyaluronic acid The term "conditions or diseases accompanying anomalous decomposition of hyaluronic acid" refers to conditions or diseases in which decomposition of hyaluronic acid is physiologically promoted as compared with a normal state. Specific examples of such conditions or diseases include arthrosis conditions such as rheumatism, osteoarthritis, psoriatic arthropathy, gout, polyarthritis, and traumatic arthritis; hepatitis, gingivitis, and malignant tumors such as cancer, in which decomposition of hyaluronic acid is abnormally promoted in the affected part. Specific examples further include cirrhosis, graft rejection, psoriasis, and sclerodermia, in which decomposition of hyaluronic acid is thought to be abnormally enhanced in the affected part, due to an increase in serum hyaluronic acid level. Specific examples further include fibrosis conditions such as cirrhosis and arteriosclerosis, in which the relevant organ assumes sclerosis by the causal disease. Specific examples further include xeroderma, dry skin, and rough skin, in which water retentivity is reduced in the affected part due to decomposition of hyaluronic acid. Specific examples further include other diseases such as nephritis, keloid, hyper-restoration, and sepsis. The hyaluronic acid decomposition-inhibiting agent of the present invention may be applied to the aforementioned conditions and diseases as a therapeutic agent for eliminating the symptoms of the disease, an ameliorating agent for mitigating the symptoms, or a preventing agent for preventing the onset of the symptoms.

Tissue-Restoring Effect

Hyaluronic acid is present at high level in an intercellular space, particularly in the derma, and contributes to moisture and elasticity of the skin. Decrease or depletion of hyaluronic acid results in dryness of the skin and formation of wrinkles. Thus, the "hyaluronic acid decomposition-inhibiting agent" of the present invention can serve as a tissue-restoring medicament for preventing wrinkle formation or the like associated with decomposition of hyaluronic acid.

In the beauty and medical fields, local injection of high-molecule sodium hyaluronate is conducted for tissue restoration such as improvement of wrinkles. However, since the injected hyaluronic acid is decomposed and metabolized in the skin, the effect thereof cannot last for a long period. When used with a known hyaluronic acid preparation, the "hyaluronic acid decomposition-inhibiting agent" of the present invention suppresses decomposition of locally injected hyaluronic acid and makes the tissue restoring (wrinkle improvement) effect long-lasting.

Also, in the field of regenerative medicine, the effect of restoring skin tissue, joint tissue, etc. provided by the "hyaluronic acid decomposition-inhibiting agent" of the present invention may be utilized. When the agent of the invention is used in artificial skin, decomposition of hyaluronic acid contained in the scaffold can be suppressed.

Joint Function-Improving Effect In diseases such as deformans arthritis and rheumatoid arthritis, the synthesis/decomposition balance of hyaluronic acid is lost, and hyaluronic acid present in the synovial membrane is depleted or decomposed to low-molecular weight species. The mechanism is known to be one cause for impaired joint function. Thus, the "hyaluronic acid decomposition-inhibiting agent" of the present invention serves as a joint function-improving agent which can suppress decomposition of hyaluronic acid in the above conditions, to thereby suppress impaired joint function. Meanwhile, the concept "improvement in joint function" refers to improvement of all the conditions in relation to joint functions such as degradation of cartilage, inflammation of synovial membrane, and pain suppression.

In the medical field, local injection of high-molecule sodium hyaluronate is conducted for improvement of joint function. However, since the injected hyaluronic acid is readily decomposed and metabolized in the joints, particularly in the aforementioned affected joints, the injection must be conducted many times. When used with a known hyaluronic acid preparation, the "hyaluronic acid decomposition-inhibiting agent" of the present invention suppresses decomposition of hyaluronic acid and makes the joint function improvement effect long-lasting.

Effect of Preventing and Treating Cancer

The KIAA1199 gene is known to be highly expressed in cells and tissues of various cancers such as breast cancer, stomach cancer, and colorectal cancer, and the gene expression is reported to be reduced through administration of an anti-cancer agent.

Also, the progress of cancer is known to be correlated with the production level and decomposition level of hyaluronic acid in various cancer tissues. It is also known that hyaluronic acid produced by cancer cells, and a low-molecule decomposition product of hyaluronic acid are involved in infiltration and metastasis of cancer, and that the infiltration and metastasis is promoted by the hyaluronic acid species.

Therefore, the "hyaluronic acid decomposition-inhibiting agent" of the present invention may be employed as an anti-cancer agent for preventing progress, metastasis, etc. of cancer via hyaluronic acid.

Cosmetic Composition

The "hyaluronic acid decomposition-inhibiting agent" of the present invention may be employed as a cosmetic composition for preventing rough skin, fine wrinkles, and dry skin, by inhibiting decomposition of hyaluronic acid in the skin.

4.2 Hyaluronic Acid Decomposition-Promoting Agent

The "hyaluronic acid decomposition-promoting agent" of the present invention is a substance or preparation which promotes the expression or activity of the KIAA1199 gene or KIAA1199 protein, whereby decomposition of hyaluronic acid is promoted via KIAA1199.

As described above, the KIAA1199 gene or the KIAA1199 protein can serve as the "hyaluronic acid decomposition-promoting agent." Similar to the case of the hyaluronic acid decomposition-inhibiting agent, the KIAA1199 gene or the KIAA1199 protein is formulated with a pharmacologically acceptable carrier or additive. The same carriers and additives as described above may also be employed.

The "hyaluronic acid decomposition-promoting agent" of the present invention may be administered perorally or parenterally, but parenteral administration is preferred. Examples of the administration method include injection, transnasal administration, transpulmonary administration, and percutaneous administration. Examples of the injection include intravenous injection, intramuscular injection, intraperitoneal injection, and subcutaneous injection. The administration method may be appropriately selected in accordance with the age and symptoms of a patient, and may be systemic or topic. Topical administration is preferred.

No particular limitation is imposed on the dose of the agent, and the unit dose is appropriately selected within, for example, a range of 0.0001 mg/kg to 1,000 mg/kg. Alternatively, the dose for one patient is appropriately selected within a range of 0.001 to 100,000 mg/body.

Prevention, treatment, and amelioration of conditions or diseases accompanying abnormally promoted production and abnormally suppressed decomposition of hyaluronic acid The term "conditions or diseases accompanying abnormally promoted production of hyaluronic acid" refers to conditions or diseases in which synthesis of hyaluronic acid is physiologically promoted as compared with a normal state. Specific examples of such conditions or diseases include psoriasis, arteriosclerosis, abnormal born formation, and myocardial infarction. The term "conditions or diseases accompanying abnormally suppressed decomposition of hyaluronic acid" refers to conditions or diseases in which decomposition of hyaluronic acid is suppressed as compared with a normal state. Specific examples include alopecia and premature alopecia, in which decomposition of hyaluronic acid is thought to be abnormally suppressed in the affected part. The hyaluronic acid decomposition-promoting agent of the present invention may be applied to the aforementioned conditions and diseases as a therapeutic agent for eliminating the symptoms of the disease, an ameliorating agent for mitigating the symptoms, or a preventing agent for preventing the onset of the symptoms.

Tuning of Tissue Restoration

In aesthetic medicine (tissue restoration) employing a hyaluronic acid topical administration preparation, the injection site is tuned through administration of a hyaluronic acid decomposition enzyme. The "hyaluronic acid decomposition-promoting agent" of the present invention may be employed in tuning of tissue restoration by hyaluronic acid (decomposition of excessively injected hyaluronic acid).

Prevention and Treatment of Hearing Impairment

The present inventors have confirmed that mutated KIAA1199 protein observed in non-syndromic hearing impairment patients also have impaired hyaluronic acid decomposition function mediated by KIAA1199. This finding suggests a certain relationship between the onset of non-syndromic hearing impairment and decomposition of hyaluronic acid decomposition mediated by KIAA1199, and possibility of suppression of the onset of hearing impairment and amelioration of the symptom thereof by promoting activity or expression of KIAA1199. Thus, the "hyaluronic acid decomposition-promoting agent" may be employed in prevention and treatment of hearing impairment.

5. Preparation for Local Administration Containing the Hyaluronic Acid Decomposition-Inhibiting Agent of the Present Invention The present invention provides "a preparation for local administration containing hyaluronic acid or a pharmacologically acceptable salt thereof or a derivative thereof, and the hyaluronic acid decomposition-inhibiting agent of the present invention."

In the aesthetic medical field, high-molecule hyaluronic acid is topically injected as a tissue restoration agent such as a wrinkle improvement agent. In the medical field, high-molecule hyaluronic acid is used as an intra-articular injection for the joint function improvement in deformans arthritis or rheumatoid arthritis. However, as described above, since the injected hyaluronic acid is readily decomposed and metabolized in the body, the effect thereof cannot last, and the patient must periodically receive the administration.

When added to a known preparation for local administration containing hyaluronic acid (high-molecule hyaluronic acid), the "hyaluronic acid decomposition-inhibiting agent" of the present invention, decomposition of hyaluronic acid in the body can be suppressed, to thereby provide a longer-lasting hyaluronic acid preparation.

In the present invention, the term "hyaluronic acid" encompasses not only hyaluronic acid but also a pharmacologically acceptable salt or derivative of hyaluronic acid such as sodium hyaluronate or cross-linked hyaluronic acid. As used herein, the term "high-molecule hyaluronic acid" refers to a hyaluronic acid species having a weight average molecular weight of 100,000 or more, preferably 500,000 or more.

The preparation containing hyaluronic acid may further contain a pharmacologically acceptable carrier. Examples of the pharmacologically acceptable carrier or additive include a surfactant, a vehicle, a colorant, a flavoring agent, a preservative, a stabilizer, a buffer, a suspending agent, a tonicity agent, a binder, a disintegrant, a lubricant, a fluidity-prompter, and a corrigent. Specific examples of the carrier which may be employed in the invention include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrroridone, gelatin, medium-chain fatty acid triglyceride, polyoxyethylene-hydrogenated castor oil 60, succharose, carboxymethylcellulose, corn starch, and inorganic salts.

Generally, the hyaluronic acid preparation is provided in the form of an ampule preparation in which a high-molecule hyaluronic acid isotonic solution containing hyaluronic acid, a tonicity agent, and a buffer is charged into an ampule, or a pre-filled preparation in which the contents are charged into a syringe or the like.

The preparation for local administration may be provided in the form of a premixture containing "hyaluronic acid or a pharmacologically acceptable salt thereof or a derivative thereof" and the "hyaluronic acid decomposition-inhibiting agent," or in the form of a kit preparation containing separate components charged in a single package. In the latter case, the preparation may be reconstituted upon use, or the components are sequentially administered.

In the "preparation for local administration" of the present invention, the ratio in amount of "hyaluronic acid decomposition-inhibiting agent" to "hyaluronic acid or a pharmacologically acceptable salt thereof or a derivative thereof" may be appropriately adjusted in accordance with the molecular weight, cross-linking degree, concentration, etc. of the hyaluronic acid employed.

The "preparation for local administration containing hyaluronic acid or a pharmacologically acceptable salt thereof or a derivative thereof and the hyaluronic acid decomposition-inhibiting agent of the present invention" of the present invention is employed as a long-lasting tissue restoration medicament, a wrinkle improvement medicament) or a joint function improvement agent. As used herein, the concept "improvement in joint function" refers to improvement of all the conditions in relation to joint functions such as degradation of cartilage, inflammation of synovial membrane, and pain suppression.

6. Hyaluronic Acid Decomposition-Controlling Agent Screening Method

The present invention provides a method for selecting a hyaluronic acid decomposition-controlling agent, targeting KIAA1199. Specifically, the hyaluronic acid decomposition controlling effect of a test substance is assessed on the basis of the expression level of the KIAA1199 gene or the KIAA1199 protein as an index. Alternatively, the hyaluronic acid decomposition controlling effect of a test substance is assessed on the basis of, as an index, the molecular weight of hyaluronic acid added to the test substance.

The screening system may be a cultured cell system or an animal model system. From the viewpoint of operational simplicity, a cultured cell system is preferred.

6.1 Assessment Method Based on the Expression Level of the KIAA1199 Gene or the KIAA1199 Protein as an Index The assessment method based on the expression level of the KIAA1199 gene or the KIAA1199 protein as an index may be carried out in the following manner:

1) culturing cells in the presence or absence of a test substance;

2) determining the expression level of the KIAA1199 gene or the KIAA1199 protein in the cells; and 3) assessing the hyaluronic acid decomposition controlling effect of the test substance on the basis of the difference between the expression level of the KIAA1199 gene or the KIAA1199 protein in the cells determined in the presence of the test substance and that determined in the absence of the test substance.

Cells

No particular limitation is imposed on the cells employed in the screening method of the present invention, so long as KIAA1199 is highly expressed transiently or stably in the cells. Cells such as fibroblasts and synovial cells may be selected. As used herein, the expression "highly expressed stably" refers to a state in which the KIAA1199 gene or protein is expressed at such a high level that the action of a test substance on KIAA1199 can be sufficiently assessed.

The cells may be cells artificially expressed through incorporating the KIAA1199 gene of the present invention into appropriate host cells. Such cells are produced by cloning cDNA of the KIAA1199 gene through a routine method and incororating the cDNA into host cells by use of an appropriate vector (see, for example, Molecular Cloning, A Laboratory Manual, Maniatis T., Fritsch E. F., Sambrook, J., Cold Spring Harbor Laboratory Press (1982)). No particular limitation is imposed on the host cells, so long as the cells can harbor a mammal gene. Examples of the cells include cells of a vertebrate animal, an insect, a yeast, etc. may be employed. Examples of the vertebrate cells which may be employed include monkey cells, COS cells (ATCC CRL-1650), Chinese hamster ovary cells (CHO cells, ATCC CCL-61), and cells of a dihydrofolic acid reducing enzyme-deficient strain thereof (see, for example, Urlaub G. and Chasin L. A., Proc. Natl. Acad. Sci. USA 77, 4126 to 4220 (1980)). Examples of the insect cells which may be employed include cells of an ovary cell-derived strain of *Lepidoptera Noctuidae, Spodoptera frugiperda* (Sf-9 or Sf-21) and *Trichoplusia ni* ovary-derived high five cells (Wickham T. J., et al., Biotechnol. Prog. i: 391 to 396 (1992)).

Alternatively, instead of the aforementioned method, expression of KIAA1199 and KIAA1199 gene can be indirectly detected by use of a reporter gene which can detect promoter activity under the control of the KIAA1199 gene promoter. Gene transfer may be transient. Alternatively, there may be also employed stable transformed cells obtained by doubly transforming host cells by use of a reporter gene and a KIAA1199 gene expression vector before selection. In the latter case, a cell strain which promotes expression of a reporter gene under the conditions where expression of the KIAA1199 gene is induced is needed. That is, cells can maintain the incorporated gene through, for example, incorporation it into a chromosome of a host cell, even after subculturing host cells, and such stable transformed cells are selected by use of an appropriate selection marker.

When cells of the thus-obtained cell strain are placed under the conditions where expression of the KIAA1199 gene is induced, transcription of the reporter gene is promoted in response to expression of the KIAA1199 gene. Thus, through measuring the expression level of the reporter gene under the conditions where expression of the reporter gene is induced, in the presence and absence of a test substance in the medium, the expression level of the KIAA1199 gene can be derived from the difference between two measurements.

Determination of the Expression Level of the KIAA1199 Gene

The expression level of the KIAA1199 gene is determined by extracting total RNA from the recovered cells and measuring the expression level of the KIAA1199 gene (mRNA) in the total RNA through any of the following methods.

No particular limitation is imposed on the total RNA extraction method, and examples of the extraction method which may be employed in the invention include guanidinium thiocyanate-cesium chloride ultracentrifugation, guanidinium thiocyanate-hot phenol method, guanidinine hydrochloride method, and acidic guanidinium thiocyanate-phenol-chloroform method (Chomczynski P. and Sacchi N., Anal. Biochem., 162, 156 to 159 (1987)). The extracted total RNA may further purified to isolate mRNA, if needed.

The gene expression level may be determined through a known method employing an immobilized sample such as a gene chip or an array, for example, nucleic acid hybridization method, RT-PCR, real-time PCR, subtraction method, differential display method, differential hybridization method, and cross-hybridization method.

Determination of Expression Level of KIAA1199 Protein

The expression level of KIAA1199 protein may be determined through, for example, an immunological assay employing antigen-antibody reaction.

Examples of the immunological assay include solid phase immunoassay methods including immunoprecipitation, western blotting, dot blotting, slot blotting, ELISA, and RIA; and known modified methods thereof (e.g., sandwich ELISA, method disclosed in U.S. Pat. No. 4,202,875, and Meager's method (Meager A., Clin, Exp. Immunol. 132(1), p. 128-36 (April, 2003)). Specifically, based on these methods, the expression level of KIAA1199 protein is determined by use of an antibody which binds specifically to KIAA1199 protein.

The anti-KIAA1199 antibody may be labeled, if needed. In labeling, the anti-KIAA1199 antibody may be directly labeled. Alternatively, the antibody is used as a primary antibody, and a labeled secondary antibody which specifically recognizes the primary antibody (which recognizes an antibody originating from the animal in which the antibody has been produced) is also used in combination. No particular limitation is imposed on preferred labeling substances, but the label is preferably an enzyme (alkaline phosphatase or horse radish peroxidase) and biotin (operation in which enzyme labeled streptavidin must be bound to biotin serving as a secondary antibody is added). A variety of commercial products; i.e., labeled antibodies (or streptavidin) are available as labeled secondary antibodies (or labeled streptavidin). In the case of RIA, an antibody labeled with a radioisotope such as $^{125}I$ is used, and measurement is performed by means of a liquid scintillation counter or a similar apparatus.

Through detection of the activity of any of the labeled enzymes, the expression level of antigen is determined. In the case where the antibody is labeled with alkaline phosphatase or horse radish peroxidase, commercial products of a substrate which develops color or emits light by the catalytic action of any of the enzymes are available.

In the case where a chromogenic substrate is used, the enzymatic activity can be visually detected through western blotting or dot/slot blotting. In a preferred procedure of ELISA, absorbance of each well is measured by means of a commercial microplate reader (measurement wavelength varying depending on the substrate) for determination. In an alternative procedure, a dilution series of the antigen for forming the aforementioned antibody is prepared and employed as a standard antigen sample, and other samples are also assayed for detection, to thereby draw a standard curve (standard antigen concentration vs. measurements). By use of the standard curve, the antigen level of another sample can be determined.

In the case where a luminescent substrate is used in western blotting or dot/slot blotting, the enzymatic activity can be detected through autoradiography employing an X-ray film or an imaging plate, or through taking a photograph by means of a disposable camera. Alternatively, the determination may be performed through densitometry or by means of a molecular imager Fx system (product of Bio-Rad). Furthermore, when a light-emitting substrate is used in ELISA, the enzymatic activity is measured by means of a light-emission microplate reader (e.g., product of Bio-Rad).

In the present invention, the "expression level of the KIAA1199 gene or the KIAA protein" is not limited to a physical quantity and encompasses equivalent quantities indirectly indicating the amount such as activity and titer (e.g., antibody titer).

Assessment

The test substance is assessed through comparison of the expression level of the KIAA1199 gene or the KIAA1199 protein in the presence of the test substance (under administration) with the expression level of the KIAA1199 gene or the KIAA1199 protein in the absence of the test substance. Alternatively, in the case where the standard values of the expression level of the KIAA1199 gene or the KIAA1199 protein have been determined, the test substance may be assessed through comparison of the expression level of the KIAA1199 gene or the KIAA1199 protein in the presence of the test substance with the standard values.

For example, when the expression level of the KIAA1199 gene or the KIAA1199 protein in the presence of the test substance significantly differs from the aforementioned standard value or from the expression level of the KIAA1199 gene or the KIAA1199 protein in the absence of the test substance, the test substance is selected as a candidate hyaluronic acid decomposition-controlling agent. As used herein, the term "significant" refers to "statistically significant" generally employed in the art and corresponds to, for example, the case of $p<0.05$.

In the case of screening of the hyaluronic acid decomposition-inhibiting agent, when the expression level of the KIAA1199 gene or the KIAA1199 protein in the presence of the test substance is significantly lower than the aforementioned standard value or than the expression level of the KIAA1199 gene or the KIAA1199 protein in the absence of the test substance, the test substance is selected as a candidate hyaluronic acid decomposition-inhibiting agent.

6.2 Assessment on the Basis of, as an Index, the Molecular Weight of Hyaluronic Acid Exogenously Added to the Test Substance The decomposition of hyaluronic acid by the mediation of KIAA1199 assessed on the basis of the molecular weight of hyaluronic acid as an index may be carried out in the following manner:

1) culturing cells in which the KIAA1199 gene is highly expressed transiently or stably in coexistence with a labeled hyaluronic acid in the presence or absence of a test substance;

2) recovering the culture supernatant after culturing and determining the molecular weight of the labeled hyaluronic acid by means of a gel filtration column; and 3) assessing the hyaluronic acid decomposition controlling effect of the test substance on the basis of the difference between the molecular weight of the labeled hyaluronic acid determined in the presence of the test substance and that determined in the absence of the test substance.

Cells in which the KIAA1199 gene is highly expressed transiently or stably may be produced through the aforementioned method.

The molecular weight of hyaluronic acid may be determined by preparing hyaluronic acid labeled with a radioisotope such as [$^3$H] through a routine method and subjecting the labeled hyaluronic acid to gel filtration or a similar process.

As described above, assessment is performed through comparison of the molecular weight of [$^3$H]-labeled hyaluronic acid in the presence of the test substance with that in the absence of the test substance. Specifically, when the molecular weight of hyaluronic acid in the presence of the test substance is significantly higher than the molecular weight of hyaluronic acid in the absence of the test substance, the test substance can be selected as a candidate hyaluronic acid decomposition-inhibiting agent. When the molecular weight of hyaluronic acid in the presence of the test substance is significantly lower than the molecular weight of hyaluronic acid in the absence of the test substance, the test substance can be selected as a candidate hyaluronic acid decomposition-promoting agent.

7. Reagent and Kit

The present invention also provides a kit for assessing the hyaluronic acid decomposition controlling effect.

The kit contains, as an essential element, at least one of the following (a) to (d):

(a) cells in which the KIAA1199 gene is highly expressed transiently or stably;

(b) a monoclonal antibody specific to a protein encoded by the KIAA1199 gene;

(c) an oligonucleotide primer for specifically amplifying the KIAA1199 gene; and (d) a polynucleotide probe for detecting the KIAA1199 gene by binding specifically to the gene.

Among these elements, components (b) to (d) each may be employed as a reagent for assessing hyaluronic acid decomposition controlling effect.

(a) Cells in which the KIAA1199 Gene is Expressed

The cells in which the KIAA1199 gene is highly expressed transiently or stably may be prepared through the aforementioned method. The cells may be recombinant cells that have been forced to express the KIAA1199 gene.

(b) Anti-KIAA1199 Monoclonal Antibody

The anti-KIAA1199 monoclonal antibody (i.e., a monoclonal antibody specific to a protein encoded by the KIAA1199 gene) is preferably an antibody which is specific to an epitope peptide having an amino acid sequence represented by any of SEQ ID NOs: 3 to 5, or which is specific to an peptide having an amino acid sequence having an identity of 90% or higher with respect thereto.

The anti-KIAA1199 monoclonal antibody may be labeled with an appropriate label (e.g., an enzyme label, a radio-label, or a fluorescent label) or appropriately modified with biotin or the like. The monoclonal antibody may be immobilized by an appropriate support, or a kit containing the monoclonal antibody may separately include a such a support so that the support can immobilize the monoclonal antibody. Examples of the support which may be used in the invention include protein-adsorbing synthetic resins such as polyethylene, polypropylene, polybutylene, polystyrene, polymethacrylate, and polyacrylamide; supports made of glass, nitrocellulose, cellulose, or agarose; and a gel-form support. No particular limitation is imposed on the form of the support, and microparticles such as ultramicro-spheres or beads (e.g., "latex" beads), tubes (inner walls) such as micro-quantity centrifugation tubes, and a micro-titer plate (wells).

(c) Primer for Amplifying the KIAA1199 Gene

The primer for amplifying the KIAA1199 gene is a continuous oligonucleotide having 5 to 30 nucleotides which has a sequence complementary to at least a part of the KIAA1199 gene. The primer may be readily designed through a routine method and amplifying. For example, the primer may be prepared according to the nucleotide sequence (SEQ ID NO: 1) for KIAA1199 gene amplification through use of commercial primer designing software. Examples of such a primer include oligonucleotides having nucleotide sequences represented by SEQ ID NOs: 9 to 13.

The KIAA1199 gene amplification primer may be labeled with an appropriate label (e.g., an enzyme label, a radio-label, or a fluorescent label) or modified with biotin, phosphoric acid, amine, or the like.

(d) Probe for Detecting KIAA1199 Gene

The KIAA1199 gene detection probe is a polynucleotide which hybridizes specifically with the KIAA1199 gene and preferably has about 20 to about 1,500 nucleotides. Specifically, in northern hybridization, a single-strand oligonucleotide or a double-strand DNA having about 20 nucleotides is suitably used. In the microarray method, a double-strand DNA having about 100 to about 1,500 nucleotides, or a single-strand oligonucleotide having about 20 to about 100 nucleotides is suitably used. When a Gene Chip system of Affimetrix is employed, a single-strand oligonucleotide having about 25 nucleotides is preferred. These oligonucleotides are preferably designed as probes which hybridize specifically with a part having high sequence specificity present in the 3'-non-translated domain of the KIAA1199 gene. Examples of such probes include oligonucleotides having nucleotide sequences represented by SEQ ID NO:s 14 to 16 in the sequence list.

The KIAA1199 gene detection probe may be labeled with an appropriate label (e.g., an enzyme label, a radio-label, or a fluorescent label) or modified with biotin, phosphoric acid, amine, or the like.

The KIAA1199 gene amplification primer and the KIAA1199 gene detection probe may be labeled with an appropriate label (e.g., an enzyme label, a radio-label, or a fluorescent label) or modified with biotin, phosphoric acid, amine, or the like. Also, the KIAA1199 gene detection probe may be fixed on an appropriate support such as a glass plate, nylon membrane, microbeads, and a silicon chip.

The kit of the present invention, containing the aforementioned components, may further contain other elements required for the detection of KIAA1199; such as a (labeled) secondary antibody specific to an anti-KIAA1199 monoclonal antibody, a reagent for detecting a labeled form, a reaction buffer, an enzyme, and a substrate. In the assessment method employing the molecular weight of hyaluronic acid as an index, hyaluronic acid labeled with a radioisotope such as [$^3$H] may be included.

EXAMPLES

The present invention will next be described in more detail by way of examples, which should not be construed as limiting the invention thereto.
[Method and Materials]
Cell Culturing Normal human skin fibroblasts (Detroit 551, ATCC (American Type Culture Collection), HS-27, NHDF) were cultured in an Eagle's minimal essential medium (MEM) (MP Biomedicals, Solon, Ohio) supplemented with essential amino acids, 1 mM sodium pyruvate, and 10% (vol/vol) fetal bovine serum (FBS) (JRH Biosciences, Kansas). HEK293, COS-7 cells, and human synovial fibroblasts (TOYOBO) were maintained in a Dulbecco's modified Eagle's medium (Sigma) containing 10% fetal bovine serum, 100-units/mL penicillin, and 100-μg/mL streptomycin. Culturing was performed at 37° C. in a humidified atmosphere containing 5% $CO_2$.
[$^3$H]-Labeled Hyaluronic Acid

[$^3$H]-labeled hyaluronic acid ([$^3$H]HA) was prepared though a slightly modified method of Underhill, Toole, et al. (C. B. Underhill and B. P. Toole, Binding of hyaluronate to the surface of cultured cells. J. Cell Biol. 82 (1979) 475-84). Specifically, confluent Detroit 551 fibroblasts were incubated with D-[1,6-$^3$H(N)]glucosamine hydrochloride (10-μCi/mL). A conditioned medium was pooled, and the incubated cells were digested with pronase (0.3 mg/mL) and precipitated in ethanol. The formed pellets were suspended in water and re-precipitated with 1.5% cetylpyridinium chloride and 0.03M NaCl. The thus-formed pellets were dissolved in 0.1% cetylpyridinium chloride and 0.4M NaCl and re-precipitated again in ethanol. The thus-formed pellets were suspended in 5 mM phosphate buffer (pH: 7.5), and the suspension was applied to a Sepharose CL-2B column (10×600 mm) equilibrated with 0.5% NaCl. Vo fractions were collected, and the product was precipitated in ethanol. Finally, the product was dissolved in 5 mM phosphate buffer (pH: 7.5).
[$^3$H]HA Decomposition Assay Using Cells Cells were cultured in a medium containing [$^3$H]HA (40,000 dpm/mL) to confluent. After incubation, the medium was removed and applied to a Sepharose CL-2B column (10×600 mm). The medium was eluted with 0.5% NaCl at 0.65 mL/min, and fractions (each 2.55 mL) were collected. The radioactivity of each fraction was measured.
Antibody Rat monoclonal antibodies to human KIAA1199 were produced through a routine method. Anti-human HYAL2 polyclonal antibodies were produced through a method of Harada, Takahashi, et al. (Hosami Harada and Masaaki Takahashi, CD44-dependent intracellular and extracellular catabolism of hyaluronic acid by hyaluronidase-1 and -2. J. Biol. Chem., 282 (2007) 5597-5607). These specific antibodies were subjected to affinity purification by use of immune peptides. An anti-CD44 antibody and GAPDH antibody were purchased from Santa Cruz Biotechnology (Santa Cruz, Calif.).

The sequences of three epitope peptides used for the production of anti-human KIAA1199 monoclonal antibodies are as follows:

```
                                           (SEQ ID NO: 3)
CDRFDTYRSKKESER, (SEQ ID NO: 4)
CARYSPHQDADPLKPRE,
and (SEQ ID NO: 5)
CDKVEQSYPGRSHYY.
```

Plasmid cDNAs of human KIAA1199, HYAL1, and HYAL2 were amplified through PCR, and each cDNA sequence was determined through DNA sequencing. Each of the thus-amplified cDNA was inserted into an expression vector pcDNA3.1(−) (Invitrogen). Transient incorporation was performed by use of Lipofectamine LTX (Invitrogen, Carlsbad, Calif.).
Stable Transformant Cells were cultured in a medium containing G418, and stable transformants were selected. Expression of KIAA1199 was confirmed through western blotting and [$^3$H]HA decomposition assay using cells.
RNA Interference siRNAs (TT2 cohesive end, non-modified) each having 25 nucleotides with respect to KIAA1199, HYAL2, CD44, and a negative control were purchased from Invitrogen (Carlsbad, Calif.). Each siRNA was incorporated by use of Lipofectamine RNAiMAX (Invitrogen, Carlsbad, Calif.).

The sequences of the three siRNAs are as follows:

```
                                           (SEQ ID NO: 6)
5'-AAACAUUGAAAUAUUCGCCAUGCUC, (SEQ ID NO: 7)
5'-UUGACAAGGAGGCCAAGACAGUGGU,
and (SEQ ID NO: 8)
5'-UUCAGCUUCAGGAACAACAGCCCUG.
```

Expression Analysis

Western blotting was performed through a standard method. In real-time PCR, total RNA was separated by use of RNeasy (Qiagen), and cDNA was synthesized by means of High Capacity cDNA Archive kit (Applied Biosystems, Foster City, Calif.). Real-time PCR was performed through Taq-Man (registered trademark) technique and by means of an apparatus ABI Prism 7700 (Applied Biosystems, Foster City, Calif.).

The sequences of 3 pairs of primer sequences employed in RT-PCR are shown in SEQ ID NOs: 9 to 13 in the sequence list.

```
                                           (SEQ ID NO: 9)
Forward(1): 5'-accatcagctggctcactct-3'

(SEQ ID NO: 10)
Reverse(1): 5'-tgtccatgcaactcaagagc-3'

(SEQ ID NO: 11)
Forward(2): 5'-gtgggttcaagacgtggagt-3'

(SEQ ID NO: 12)
Reverse(2): 5'-tctatctcctccccgatgtg-3'

(the same as forward (1), SEQ ID NO: 9)
Forward(3): 5'-accatcagctggctcactct-3'

(SEQ ID NO: 13)
Reverse(3): 5'-cctcctttaccaacccaat-3'
```

In situ hybridization was performed through a routine method by use of a probe represented by SEQ ID NOs: 14 to 16 in the sequence list (Probe(1): SEQ ID NO: 14, Probe(2): SEQ ID NO: 15, Probe(3): SEQ ID NO: 16).

Determination of Hyaluronic Acid Decomposition Property with Cells

Cells were cultured in a medium (PG Research) containing fluoreceinamine-labeled (FA-) HA, chondroitin sulfate A, chondroitin sulfate D, chondroitin sulfate E, dermatan sulfate, heparin, and heparan sulfate. After incubation, the medium was removed and applied to a PBS-equilibrated Sepharose CL-6B column (10×35 mm). The applied matter was eluted at 0.4 mL/min, and fractions (each: 1.6 mL) were collected. The fluorescence of each fraction was measured (excitation: 490 nm, emission: 525 nm). The molecular weight of the decomposed FA-HA was estimated from molecular weight of that of FA-chondroitin sulfate D, chondroitin sulfate E, heparin, and heparan sulfate determined under the same conditions. The non-reducing end sugar of the decomposed [$^3$H]HA was identified through gel filtration by means of a Sepadex G-25 column (1×107 cm) after incubation with β-N-acetylglucosaminidase (to the sugar chain) or after digestion with β-glucuronidase and subsequent digestion with β-N-acetylglucosaminidase.

Inhibitor Experiment

Cells were incubated for 3 hours with an inhibitor at a predetermined concentration and then incubated for 6 hours with [$^3$H]HA in the presence of the inhibitor.

[Experiments and Results]

1. Identification of Hyaluronic Acid Decomposition Factor, KIAA11199

(1) Hyaluronic Acid Decomposition System in Cultured Human Normal Fibroblasts

Firstly, whether or not the currently proposed hyaluronic acid decomposition model by the mediation of HYAL1, HYAL2, and CD44 (HA receptor) actually functions in normal cells was investigated by use of cultured human normal fibroblasts.

As a result, cultured fibroblasts decomposed exogenously added high-molecule hyaluronic acid, and the metabolites were accumulated outside the cells (FIG. 1a).

When hyaluronic acid was incubated with the medium in which fibroblasts had been cultured, no decomposition of hyaluronic acid was observed. The cells were incubated with hyaluronic acid at various concentrations thereof, and apparent Vmax (370 μg/10$^5$ cells/3 days) and Km (1,480 μg/mL) of decomposition of hyaluronic acid by cultured fibroblasts were determined (data not shown). The data suggest that cultured fibroblasts have an effective hyaluronic acid decomposition mechanism.

(2) Identification of KIAA1199

Figure 1B:
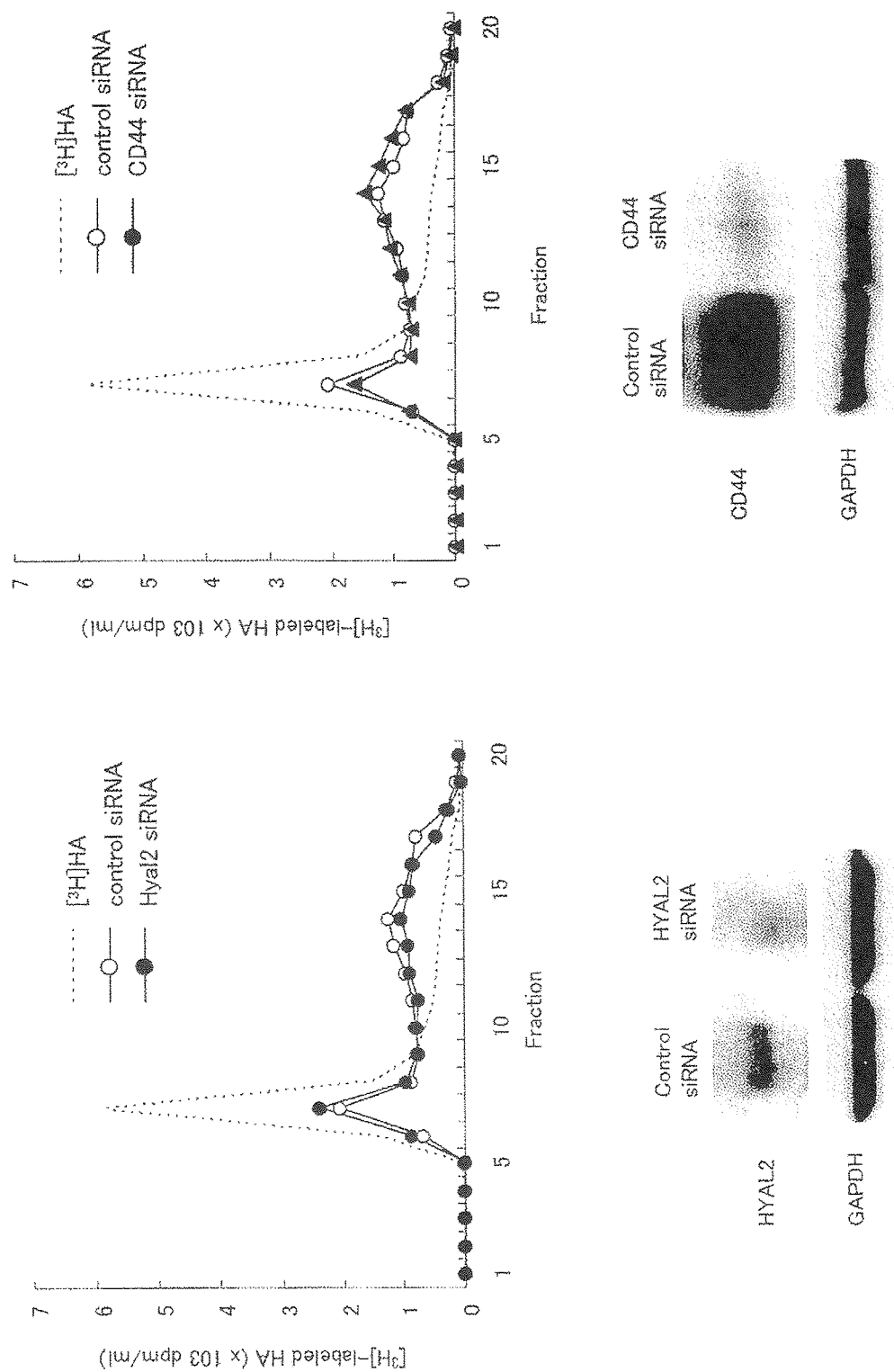
FIG. 1b Behavior of HA decomposition in cultured normal human skin fibroblasts (Detroit551) in knocking down of HYAL2 or CD44 by use of siRNA (top); and detection of expression of HYAL2 protein or CD44 protein through western blotting (bottom).

Among HYAL1, HYAL2, and CD44, expression of HYAL2 and CD44 was detected in the case of cultured fibroblasts. However, HYAL2 and CD44 knocked down with an siRNA did not affect decomposition of hyaluronic acid (FIG. 1b). Therefore, it is suggested that the hyaluronic acid decomposition mechanism of cultured fibroblasts does not depend on an HYAL enzyme or CD44.

Although the presence of a hyaluronic acid decomposition mechanism was confirmed in certain cells, no hyaluronic acid decomposition activity was detected in a fibroblast lysate under neutral pH conditions (data not shown), as disclosed in Prior Art Documents.

As shown in FIG. 1a, decomposition of hyaluronic acid was up-regulated by histamine and down-regulated by TGF-[3]. Through microarray analysis, 25 genes which can be up-regulated by histamine at a percent variation twice or slightly more and which can be down-regulated by TGF-J31 at a percent variation ½ or slightly less in fibroblasts were selected.

Figure 1C:
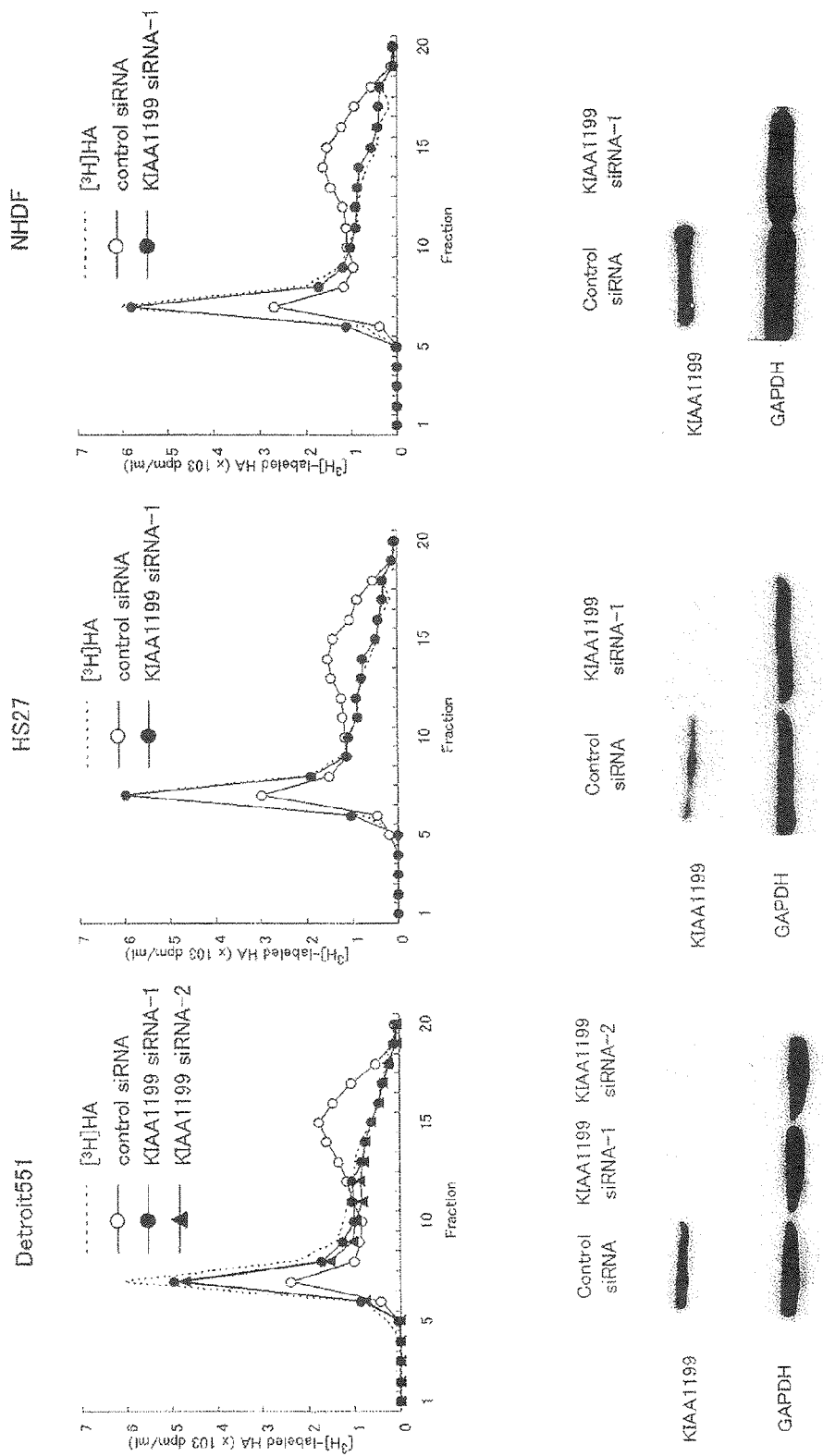
FIG. 1c Relationships between knocking down of KIAA1199 by use of one or two siRNAs in cultured normal human skin fibroblasts (Detroit551 (left), HS27 (center), and NHDF (right)) and decomposition of HA.
Figure 1D:
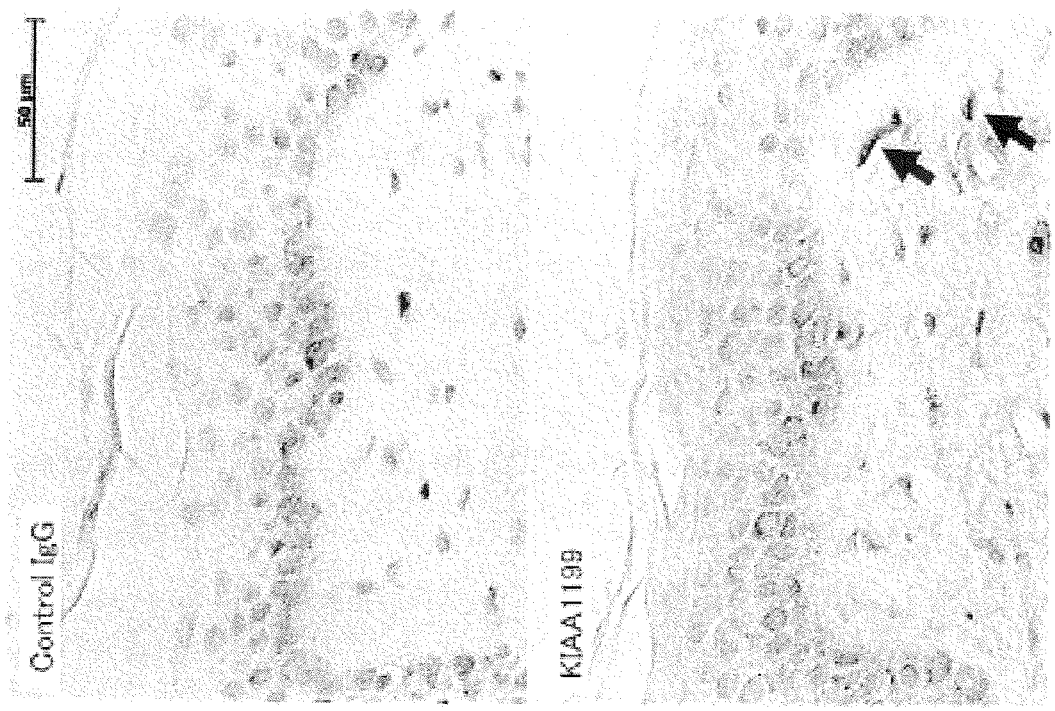
FIG. 1d Expression of KIAA1199 in human skin (left: western blotting, right: immunostaining), wherein the arrows indicate sites stained by a KIAA1199 antibody.
Figure 1D:
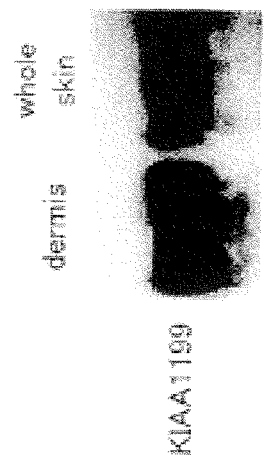
Figure 1E:
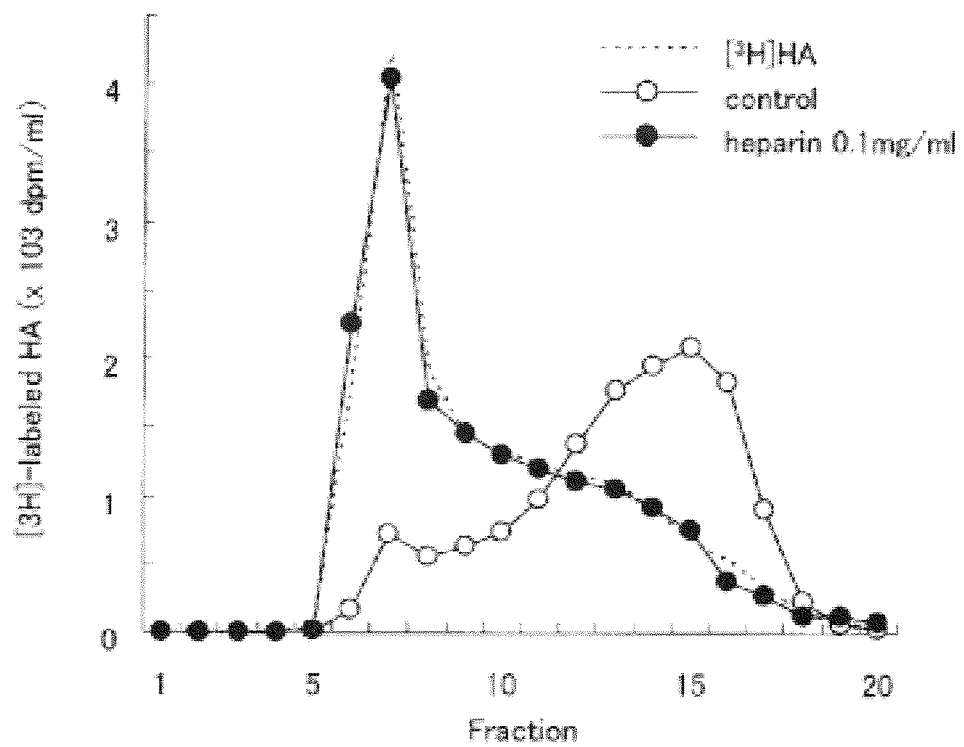
FIG. 1e Inhibition of HA decomposition in cultured normal human skin fibroblasts by heparin.

The 25 genes were sequentially knocked down. As a result, decomposition of hyaluronic acid by cells was considerably inhibited through incorporation of two siRNAs targeted to the KIAA1199 gene (FIG. 1c). The same results were obtained when other normal fibroblasts HS27 and NHDF in the skin were used (FIG. 1c). Through real-time PCR and western blotting, variation in the expression level of KIAA1199 mRNA and the KIAA1199 protein due to histamine and TGF-β1 was confirmed (FIG. 1a). After stimulation with histamine, the apparent Km of hyaluronic acid decomposition by cells was not changed (1,500 μg/mL), but Vmax 3.7-times increased (1,370 μg/10$^5$ cells/3 days). The results corresponded to the increase in expression level of KIAA1199 mRNA by stimulation with histamine (3.7 times) (FIG. 1a). Furthermore, decomposition of hyaluronic acid in cultured fibroblasts was inhibited by addition of heparin (FIG. 1e).

Thus, KIAA1199 was confirmed to be an important factor in determination of the hyaluronic acid decomposition rate in cultured fibroblasts.

In western blotting by use of an anti-KIAA1199 monoclonal antibody, a KIAA1199 protein having a molecular weight of about 150 kDa was detected in a normal human skin lysate. This coincides with the results of the experiment of cultured skin fibroblasts (FIG. 1d). Through an immunohistochemical test (immunostaining) of a normal human skin section by ues of the same antibody, expression of KIAA1199 was detected in skin fibroblasts (FIG. 1d).

2. Determination of Function of KIAA1199

(1) Decomposition of HA by KIAA1199

Figure 2A:
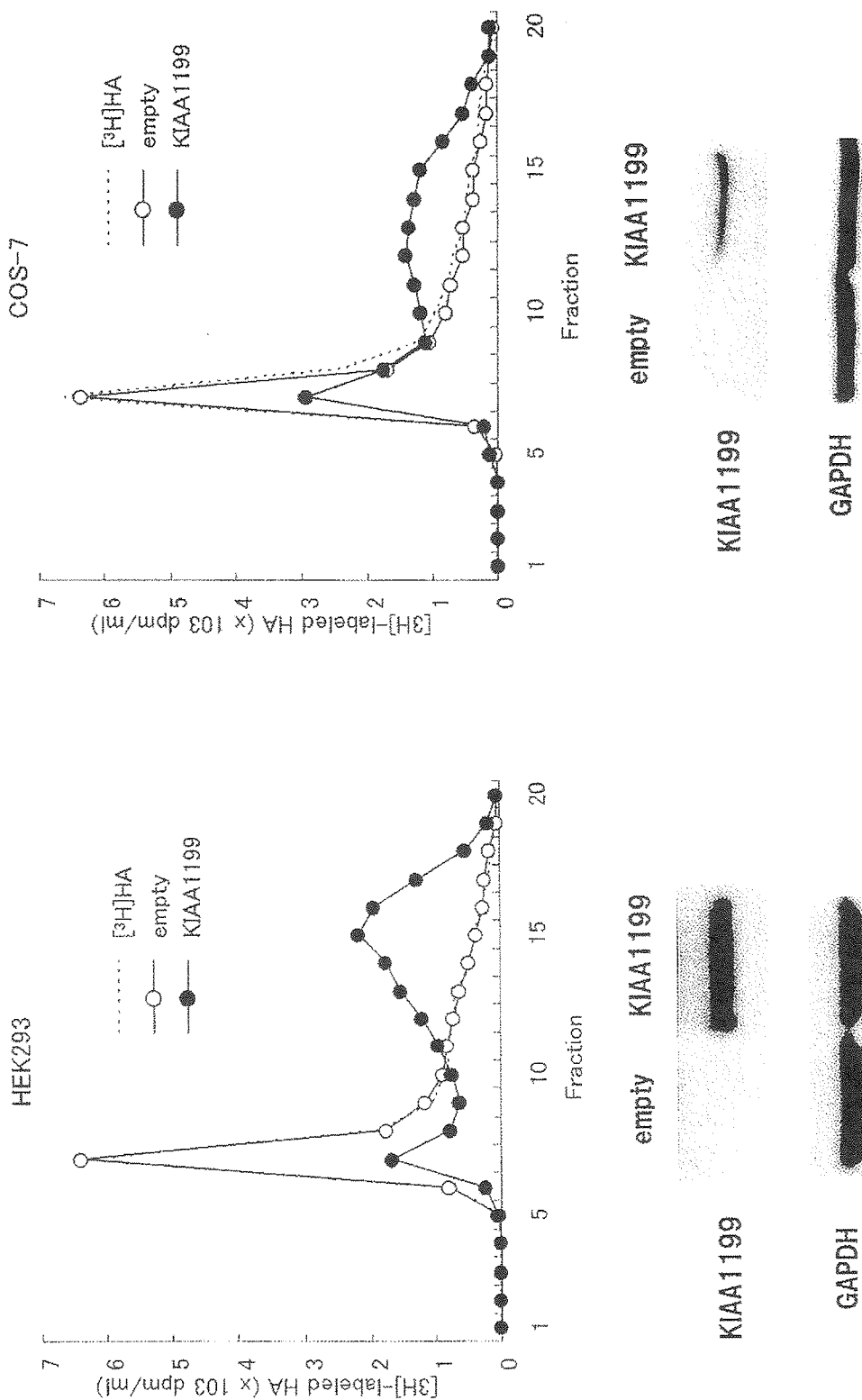
FIG. 2a Decomposition of HA added to cells in which KIAA1199 has been artificially expressed (left: HEK293, right: COS-7), and expression of KIAA1199 (western blotting), wherein circles (empty) represent empty vector-incorporated cells, and black dots (KIAA1199) represent KIAA1199-artificially expressed cells.

In order to investigate the functions of KIAA1199, a full-length cDNA of KIAA1199 was incorporated into HEK293 cells (human fetal kidney cells). Similar to cultured skin fibroblasts, HEK293 cells in which KIAA1199 are transiently expressed decomposed hyaluronic acid added to the cells (FIG. 2a). In contrast, similar cells into which a vacant vector had been incorporated did not decompose hyaluronic acid (FIG. 2a). Similar results were obtained in the case of COS-7 cells (monkey kidney fibroblasts) (FIG. 2a). As a result, it was suggested that KIAA1199 is an essential factor in the hyaluronic acid decomposition mechanism.

The cDNA sequence of KIAA1199 includes a deduced ORF of 4,083 bp encoding a protein of 1,361 amino acids. KIAA1199 exhibits no substantial homology to HYAL enzymes, bacterial hyaluronidase, and other known proteins including hyaluronic acid-bound proteins.

(2) Decomposition of HA by Mutated KIAA1199

In non-syndromic hearing impairment patients showing high-frequency dominant hearing impairment, mutations of KIAA1199 accompanying amino acid substitution (R187c, R187H, H783R, and V1109I) were detected. These mutations are reported to possibly cause hearing impairment (as described above).

Figure 2B:
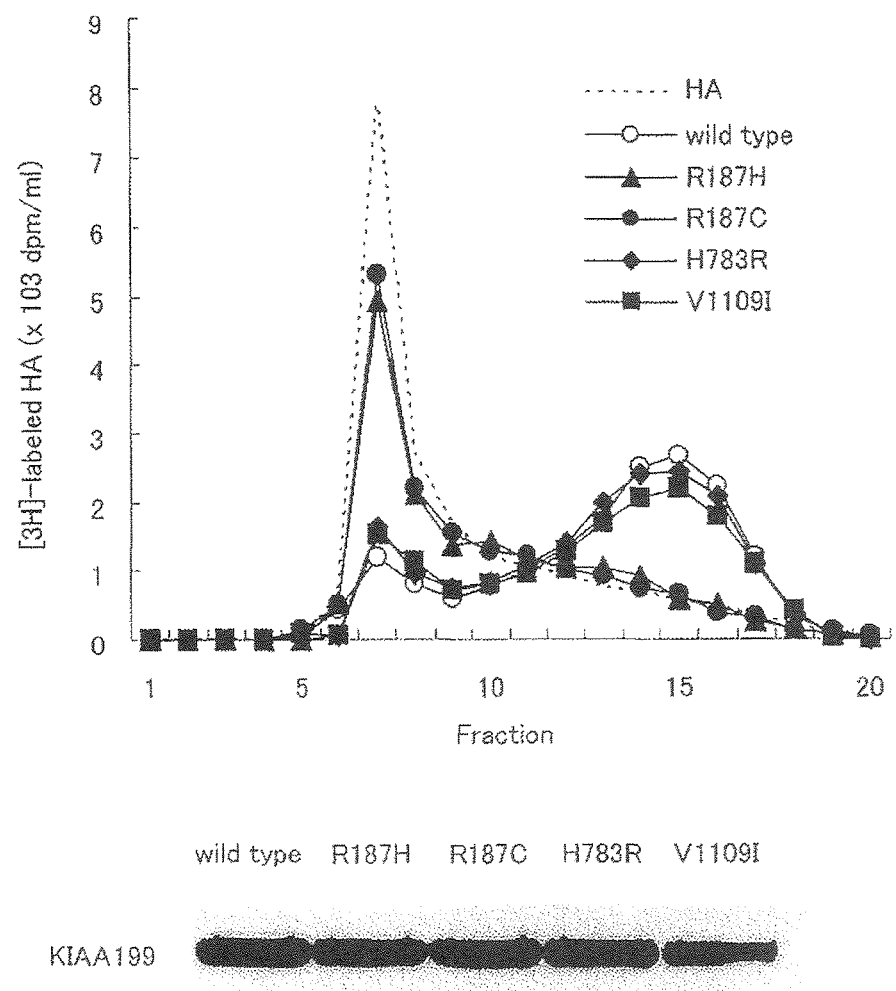
FIG. 2b Decomposition of HA by mutated KIAA1199s (triangle: R187H, circle: R187c, diamond: H783R, square: V1109I) and wild-type KIAA1199 (empty circle), which are known to relate to hearing impairment.

Thus, the four mutated KIAA1199, which had been expressed in the hearing impairment patients, were transiently produced in HEK293 cells. The four mutated KIAA1199 proteins (R187c, R187H, H783R, and V1109I) were expressed at a frequency almost the same as that of the wild-type (FIG. 2b). Among these mutants, cells in which R187C mutant or R187H mutant was expressed exhibited slightly reduced decomposition of hyaluronic acid as compared with the wild-type (FIG. 2b). The fact suggests that amino acid substitution in R187 would impair the function of KIAA1199 protein.

3. Studies on the Mechanism of Decomposition of Hyaluronic Acid by KIAA1199

Figure 3A:
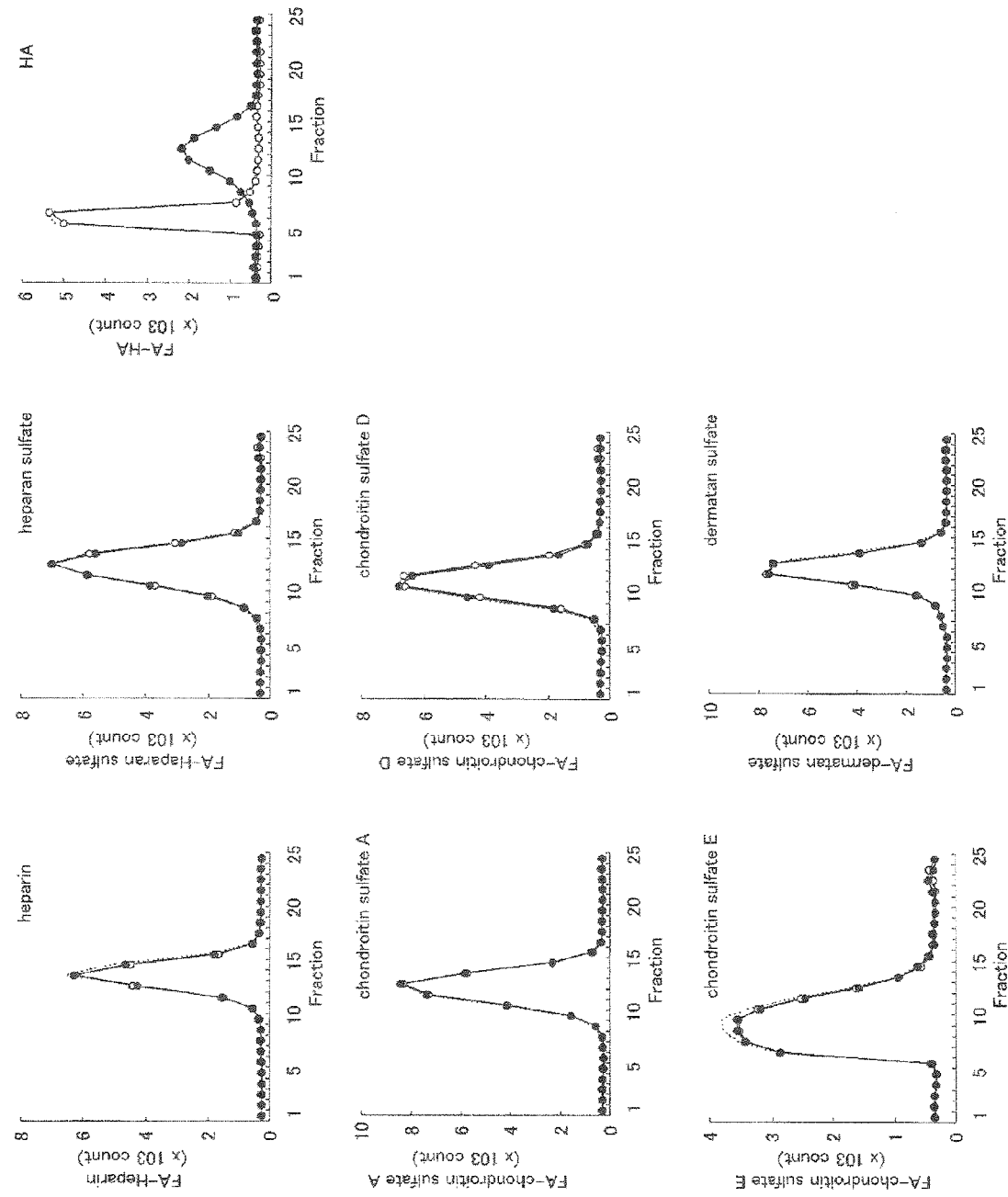
FIG. 3a Action of KIAA1199 on HA and other glycosaminoglycans (heparin, heparan sulfate, chondroitin sulfates A, D, and E, and dermatan sulfate).
Figure 3B:
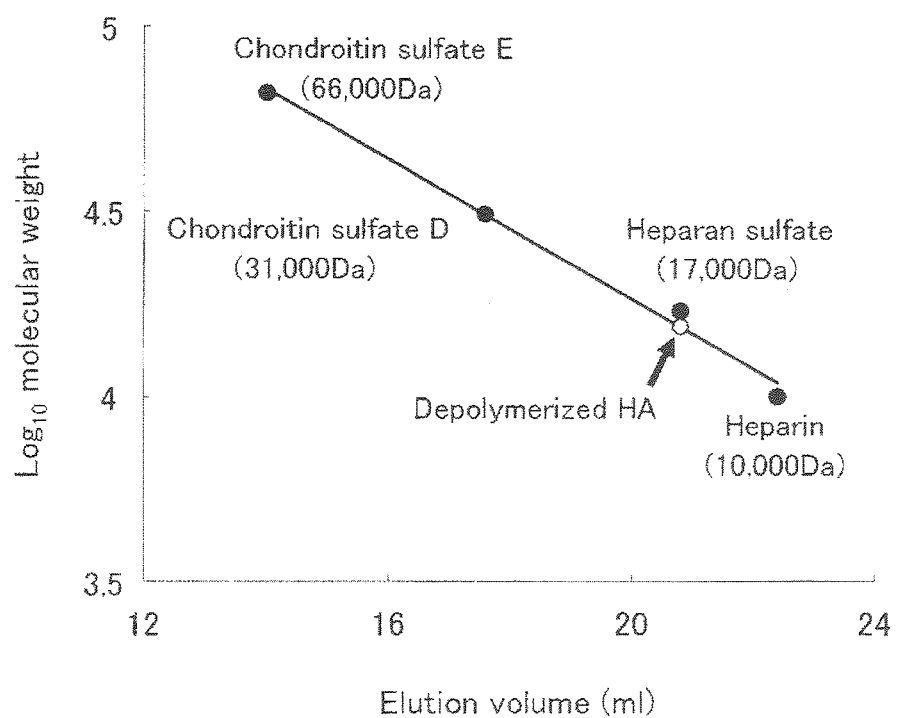
FIG. 3b Sizes of products decomposed by KIAA1199 (decomposition product: low-molecular-weight HA having an average molecular weight of about 15,000).

In order to investigate the hyaluronic acid decomposition mechanism by the mediation of KIAA1199, HEK293 cells (KIAA1199/HEK293), in which KIAA1199 is consistently expressed, were established. Differing to hyaluronic acid, cultured KIAA1199/HEK293 cells did not digest chondroitin sulfate A, D, and E, dermatan sulfate, heparin, or heparan sulfate added to the cells (FIG. 3a). The thus-decomposed hyaluronic acid was assumed to have a molecular weight of about 15 kDa (FIG. 3b), and a reducing and non-reducing end thereof were found to be N-acetylglucosamine and glucuronic acid, respectively.

The KIAA1199/HEK293 cells decomposed hyaluronic acid-specific end-β-N-acetylglucosaminidase and hyaluronic acid. The metabolites thereof were found to be medium-size hyaluronic acid fragments. Since overexpression of HYAL1 and HYAL2 in the KIAA1199/HEK293 cells did not affect decomposition of hyaluronic acid, it is suggested that KIAA1199 acts independent of HYAL1 and HYAL2.

Figure 3C:
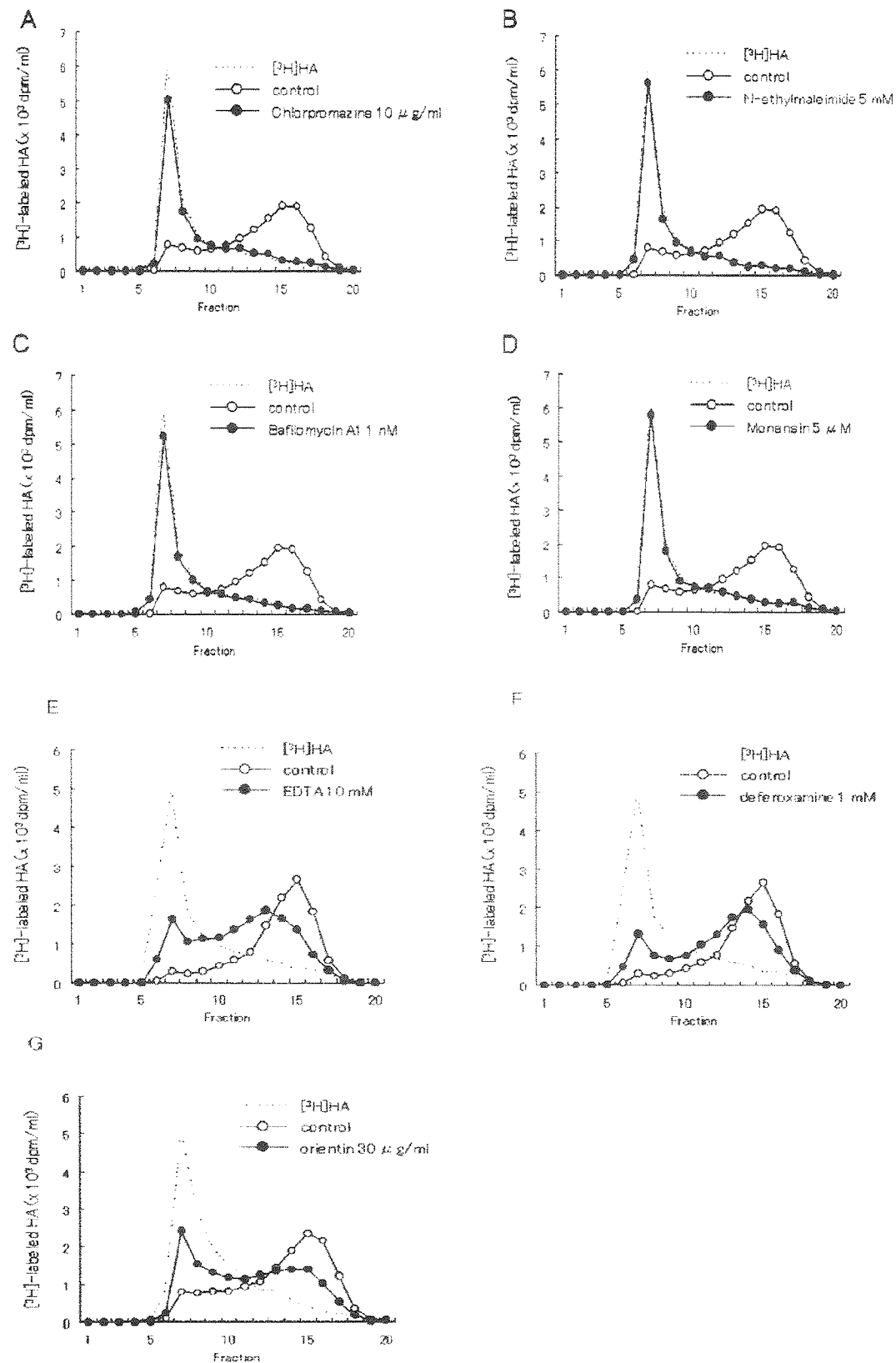
FIG. 3c Inhibition of HA decomposition by endocytosis inhibitor and lysosome function inhibitor in KIAA1199-artificially-expressed HEK293 cells (A: chlorpromazine, B: N-ethylmaleimide, C: bafilomycin Al, D: monensin, E: EDTA, F: deferoxamine, G: orientin).

Decomposition of hyaluronic acid in KIAA1199/HEK293 cells was inhibited through preliminary treatment with chlorpromazine, N-ethylmaleimide, bafilomycin A1, monensin, EDTA, deferoxamine, or orientin (FIG. 3c).

4. Involvement of KIAA1199 in Osteoarthritis (OA) and Rheumatoid Arthritis (RA)

Synovial fluid in patients of osteoarthritis (OA) or rheumatoid arthritis (RA) is known to contain a large amount of hyaluronic acid having low molecular weight and low concentration, as compared with synovial fluid from sampled from normal knee joints.

In order to confirm the involvement of KIAA1199 in the observations, normal synovial fibroblasts, cultured synovial fibroblasts originating from an OA patient, and cultured synovial fibroblasts originating from an RA patient.

Figure 4A:
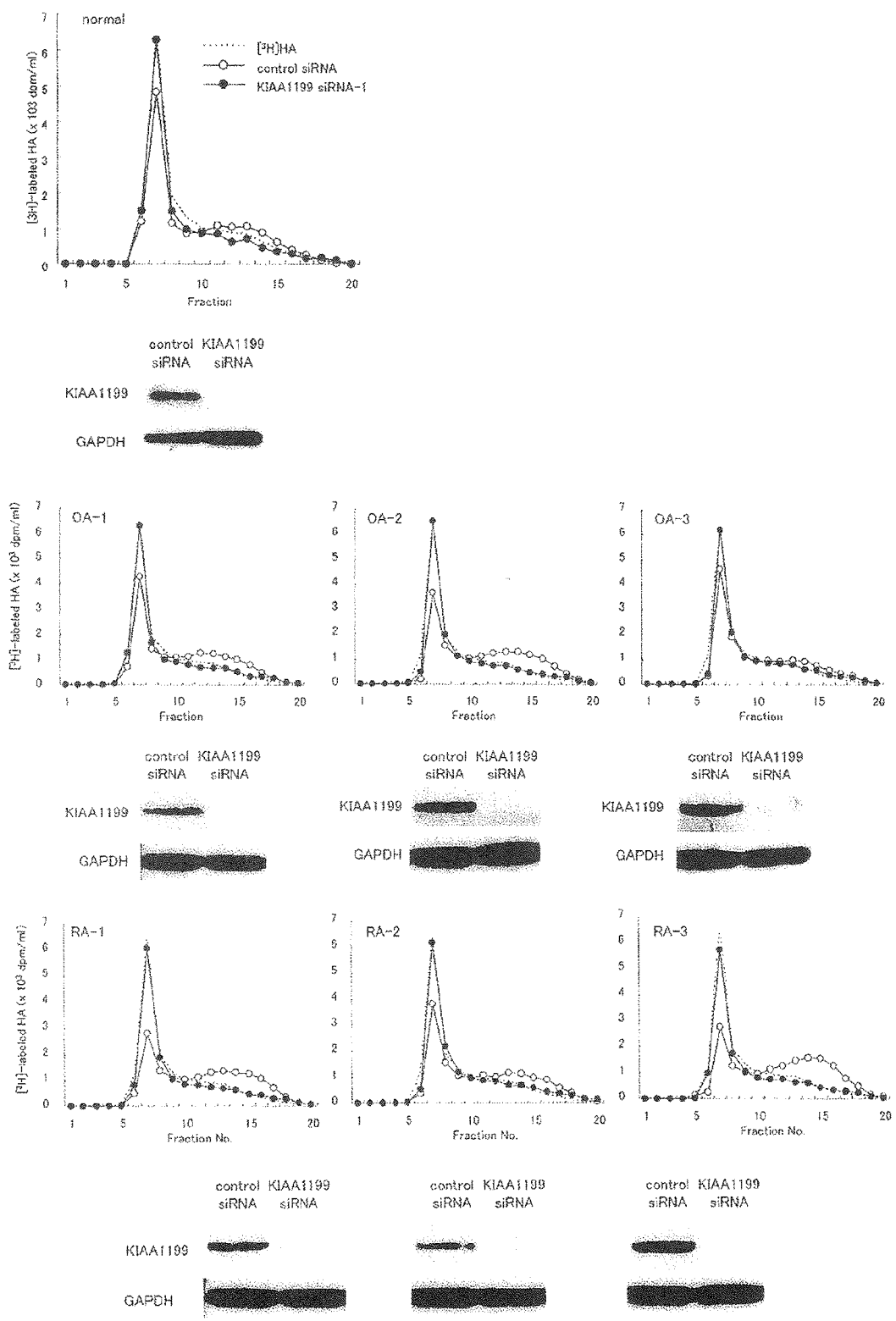
FIG. 4a Effects of knocking down of KIAA1199 by siRNA on decomposition of HA exogenously added to the cells (cultured normal synovial cells, cultured synovial cells derived from OA patients (OA-1, OA-2, and OA-3), and cultured synovial cells derived from RA patients (RA-1, RA-2, and RA-3)), wherein circle (empty) control represents non-specific siRNA-introduced cells, and black dot KIAA1199 represents KIAA1199-specific siRNA-introduced cells.
Figure 4B:
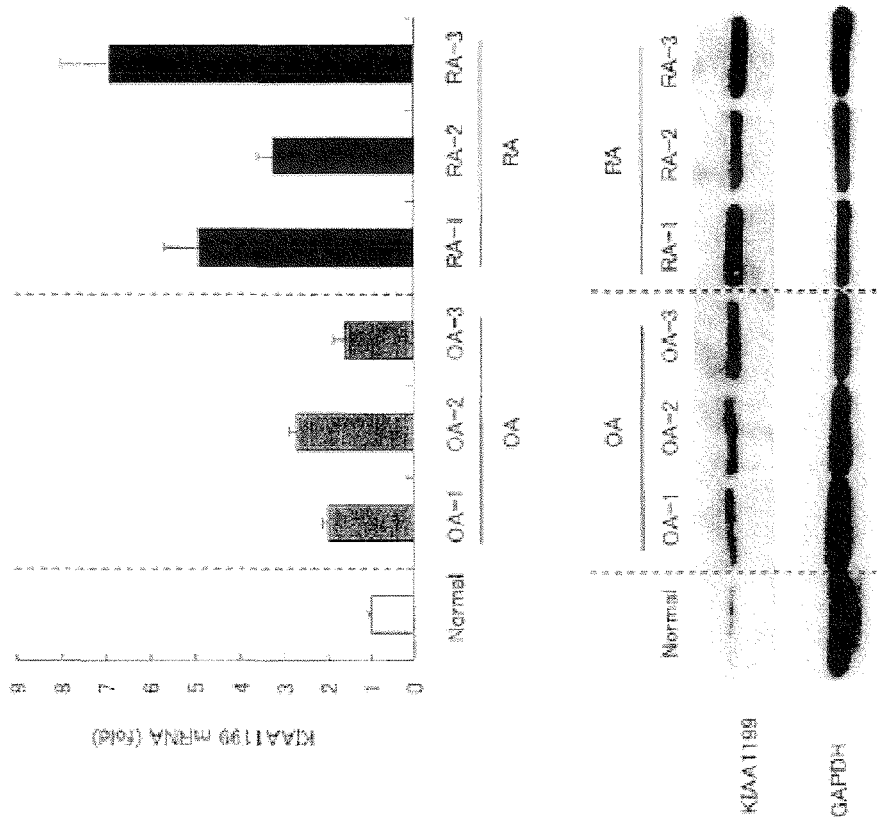
FIG. 4b Expression of KIAA1199 in the cells (cultured normal synovial cells, cultured synovial cells derived from of OA patients (OA-1, OA-2, and OA-3), and cultured synovial cells derived from RA patients (RA-1, RA-2, and RA-3).

All types of cells decomposed hyaluronic acid added to the cells. However, through knocking down KIAA1199 by a specific siRNA, decomposition was completely suppressed (FIG. 4a). Decomposition of hyaluronic acid by the cells, expression of KIAA1199 mRNA, and KIAA1199 protein were most promoted particularly in the case of synovial fibroblasts originating from an RA patient (FIGS. 4a, 4b). OA cells exhibited the promotion degree between that obtained normal cells and that obtained by RA cells (FIGS. 4a, 4b). Thus, KIAA1199 is involved in decomposition of hyaluronic acid by cultured synovial fibroblasts, and that an increase in expression amount of KIAA1199 promotes decomposition of hyaluronic acid by synovial cells originating from an OA patient or synovial cells originating from an RA patient.

Meanwhile, PGE2 (i.e., an inflammatory mediator) and several cytokines such as IL-1, IL-6, and TNF-α are present at high levels in synovial fluid of RA patients. Therefore, whether or not expression of KIAA1199 in RA synovial cells is induced by such an inflammatory mediator was investigated. As shown in FIG. 4f, PGE2, IL-1α, IL-β, and IL-6 were found to stimulate expression of KIAA1199 mRNA. That is, an RA-related inflammatory mediator can stimulate expression of KIAA1199 mRNA in RA synovial cells.

Figure 4C:
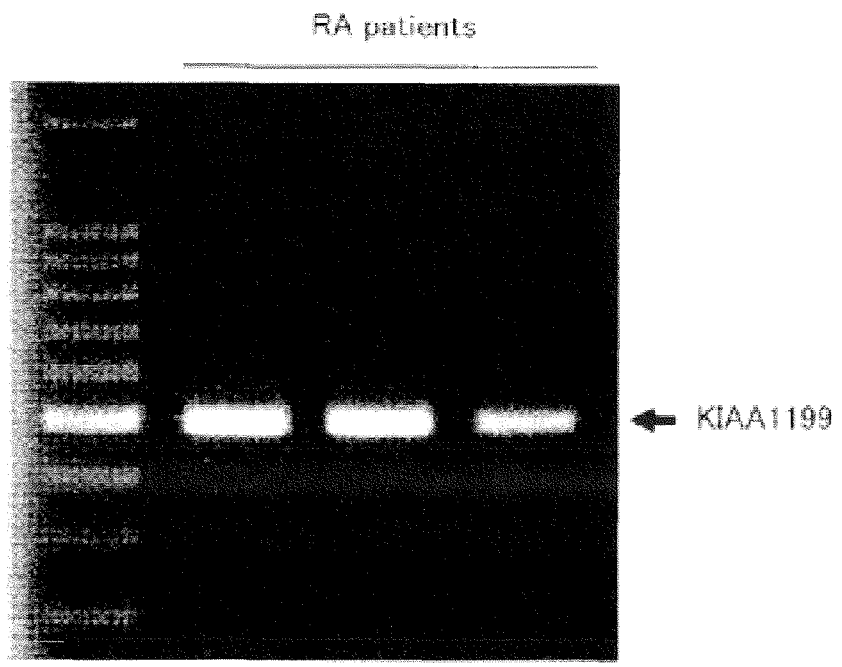
FIG. 4c Expression of KIAA1199 in the tissue of an RA patient (RT-PCR).
Figure 4D:
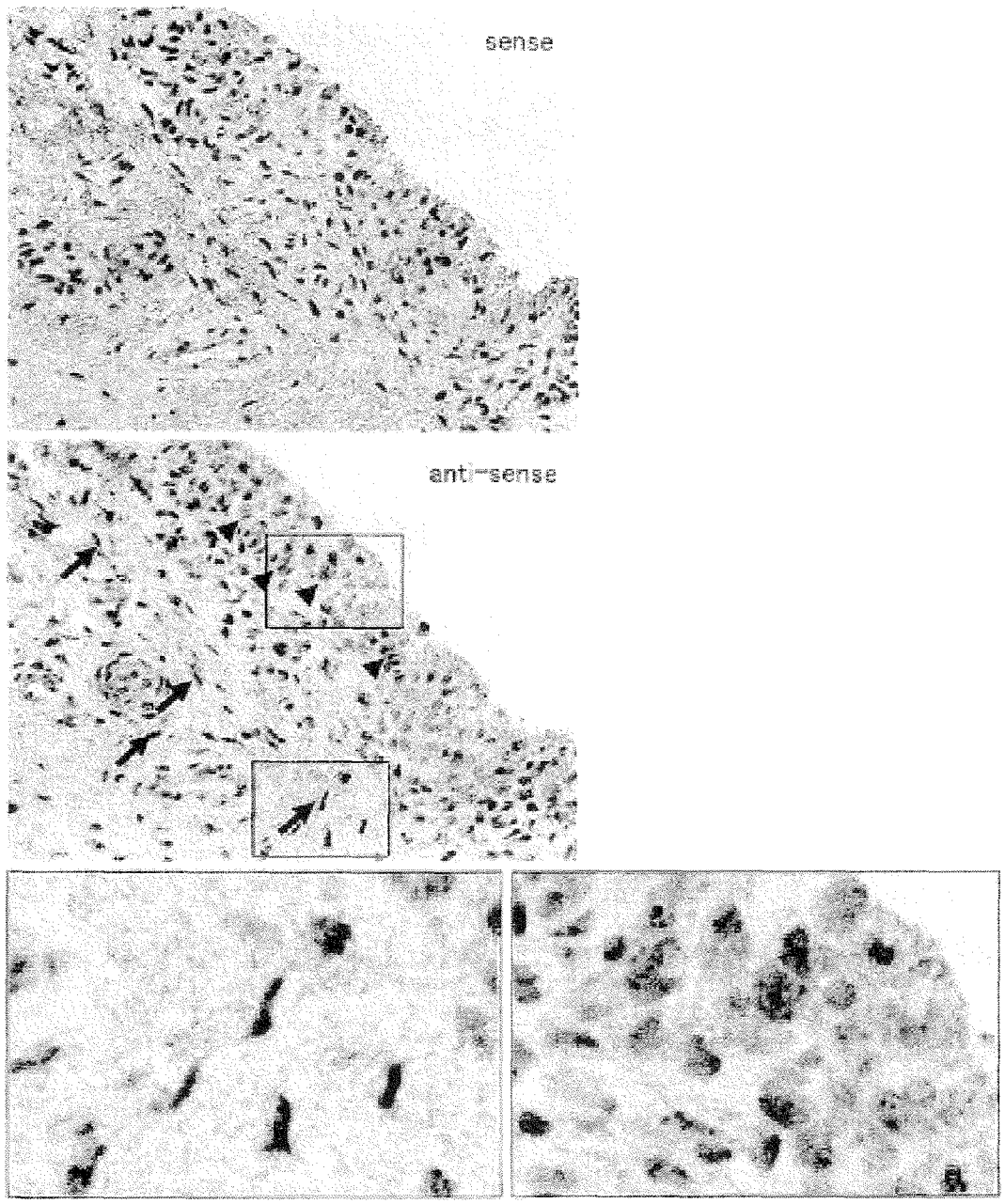
FIG. 4d Expression of KIAA1199 in the tissue of an RA patient (in situ hybridization), wherein the arrows indicate KIAA1199-localized sites.
Figure 4E:
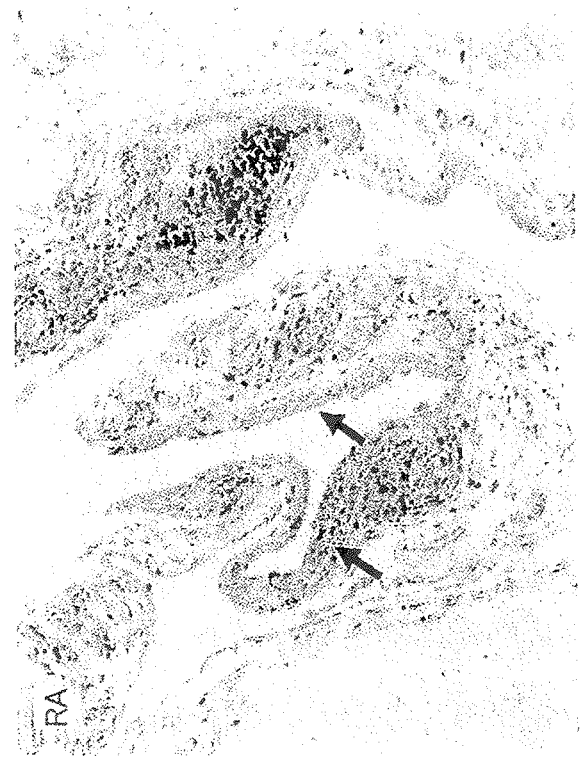
FIG. 4e Expression of KIAA1199 in the tissue of an RA patient (immunostaining), wherein the arrows indicate sites stained by a KIAA1199 antibody.
Figure 4F:
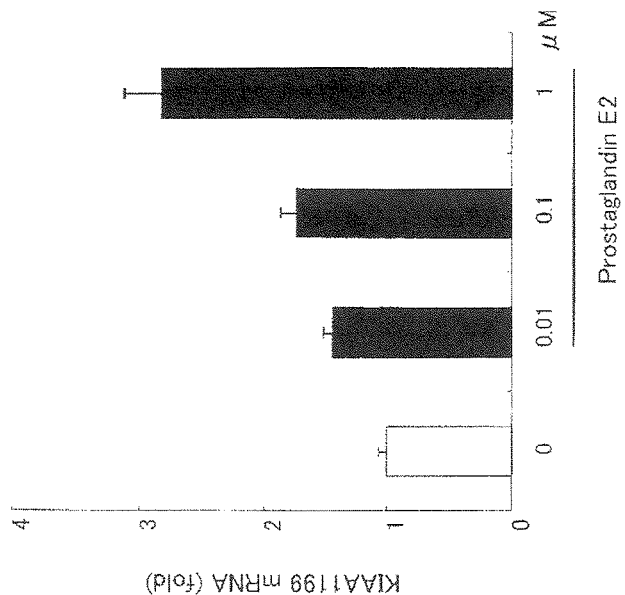
FIG. 4f Induction of KIAA1199 expression by inflammatory mediators (PGE2, interleukin (IL)-1, and IL-6) in cultured RA synovial cells.
Figure 4F:
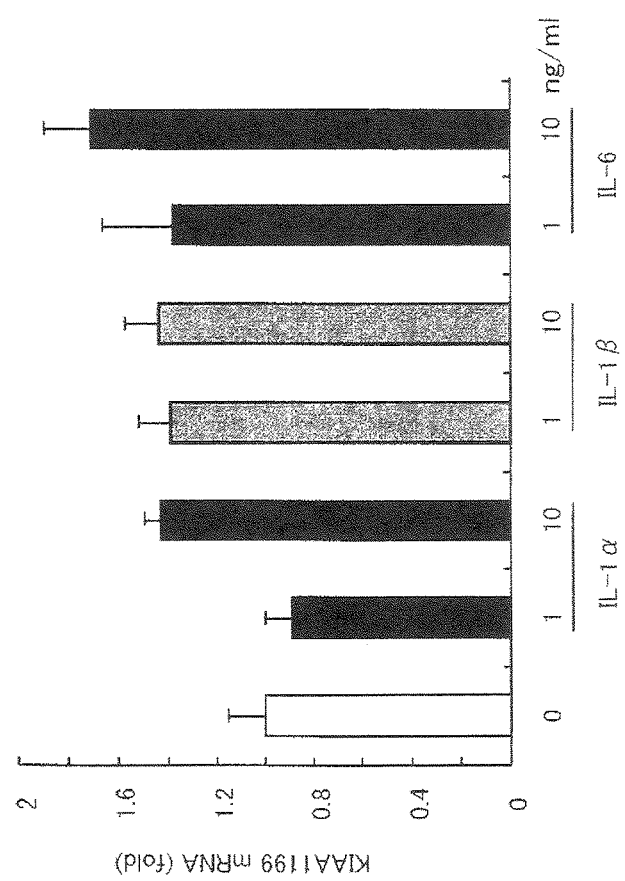

In fact, expression of KIAA1199 mRNA was detected, through RT-PCR, in the total DNA samples obtained from synovial membranes of three different RA patients (FIG. 4c). Through in situ hybridization, KIAA1199 mRNA was detected in superficial synovial cells and RA surface synovial cells (FIG. 4d). These patterns were identified at protein level through an immunohistochemical test employing an anti-KIAA1199 monoclonal antibody. The analysis revealed that KIAA1199 is expressed most effectively in RA superficial synovial cells, and the expression level is considerably higher than that observed in healthy subjects (FIG. 4e).

As described above, KIAA1199 has been confirmed to serve as a novel hyaluronic acid decomposition-promoting factor. KIAA1199 is present in a wide range of tissues, and provides a novel hyaluronic acid metabolic system in the body, which differs from a known model. In RA synovial membrane, KIAA1199 expression, which is essential for decomposition of hyaluronic acid in cultured RA synovial fibroblasts, was promoted in surface synovial cells, which is in contact with synovial fluid. This promotion suggests a relation to reduction of synovial fluid level and molecular weight of hyaluronic acid, which is one known molecular-related characteristics of RA. This finding could lead to novel elucidation of the cause of RA.

KIAA1199 is known to increase in colorectal cancer and stomach cancer. A partially metabolized hyaluronic acid fragment is known to promote angiogenesis and stimulate production of an inflammatory cytokine, which is a key to the progress of cancer. Therefore, KIAA1199 is thought to relate to such progress and metastasis of cancer. In other words, inhibition of activity and expression of KIAA1199 can be employed as a promising strategy for the treatment of RA and prevention of progress of cancer.

Meanwhile, mutation (amino acid) at R187 of KIAA1199, which is a potential cause of non-syndromic hearing impairment, impaired a function of KIAA1199. This finding also suggests that suppressed decomposition of hyaluronic acid could cause impaired sense of hearing. The finding has first suggested the relationship between the metabolism of hyaluronic acid and auditory function. That is, the present invention can provide novel means for elucidating the mechanism of auditory sense.

INDUSTRIAL APPLICABILITY

The present invention can be employed for mitigation and treatment of diseases and conditions, which would otherwise be caused by exhaustion of hyaluronic acid or reduction in molecular weight of hyaluronic acid. Also, the hyaluronic acid decomposition-inhibiting agent of the present invention can provide a longer-lasting preparation in combination with a hyaluronic acid preparation for local injection, which is used in the treatment of osteoarthritis or rheumatoid arthritis and in the beauty and medical fields. Furthermore, the present invention can be employed for retrieval of a novel hyaluronic acid decomposition-controlling agent targeted to KIAA1199 and elucidation of the mechanism of a pathological condition caused by decomposition of hyaluronic acid.

All the documents, patent publications, and patent applications cited in the specification are incorporated herein by reference.

SEQUENCE LIST FREE TEXT

SEQ ID NO: 3-human KIAA1199 epitope peptide (1)
SEQ ID NO: 4-human KIAA1199 epitope peptide (2)
SEQ ID NO: 5-human KIAA1199 epitope peptide (3)
SEQ ID NO: 6-human KIAA1199 siRNA (1)
SEQ ID NO: 7-human KIAA1199 siRNA (2)
SEQ ID NO: 8-human KIAA1199 siRNA (3)
SEQ ID NO: 9-human KIAA1199 amplification primer (Forward (1), Forward (3))

SEQ ID NO: 10-human KIAA1199 amplification primer (Reverse (1))
SEQ ID NO: 11-human KIAA1199 amplification primer (Forward (2))
SEQ ID NO: 12-human KIAA1199 amplification primer (Reverse (2))
SEQ ID NO: 13-human KIAA1199 amplification primer (Reverse (3))
SEQ ID NO: 14-human KIAA1199 detection probe (1)
SEQ ID NO: 15-human KIAA1199 detection probe (2)
SEQ ID NO: 16-human KIAA1199 detection probe (3)

What is claimed is:

1. A method for screening for an agent that modulates hyaluronic acid decomposition comprising the following steps:

A) culturing cells, which highly express the KIAA1199 gene transiently or stably, in the presence and absence of a test substance;

B) determining the expression level of the KIAA1199 gene or a protein encoded by the KIAA1199 gene in the cells; wherein a difference between the expression level of the KIAA1199 gene or the protein encoded by the KIAA1199 gene in the cell culture in the presence of the test substance and the cell culture in the absence of the test substance indicates that the test substance modulates hyaluronic acid decomposition.

2. A method for screening for an agent that modulates hyaluronic acid decomposition comprising the following steps:

A) culturing cells, which highly express the KIAA1199 gene transiently or stably, in coexistence with a labeled hyaluronic acid in the presence and absence of a test substance;

B) recovering a cultured supernatant after culturing, and determining a molecular weight of the labeled hyaluronic acid;

wherein a difference in the molecular weight of the labeled hyaluronic acid between the sample cultured in the presence of the test substance and the sample cultured in the absence of the test substance indicates that the test substance modulates hyaluronic acid decomposition.

3. The method according to claim 1, wherein the cells are recombinant cells that have been forced to express the KIAA1199 gene.

4. The method according to claim 2, wherein the cells are recombinant cells that have been forced to express the KIAA1199 gene.

\* \* \* \* \*

SEQUENCE LISTING

```
<160> NUMBER OF SEQ ID NOS: 16

<210> SEQ ID NO 1
<211> LENGTH: 7080
<212> TYPE: DNA
<213> ORGANISM: Homo sapiens
<220> FEATURE:
<221> NAME/KEY: CDS
<222> LOCATION: (261)..(4346)
<223> OTHER INFORMATION:

<400> SEQUENCE: 1
gagctagcgc tcaagcagag cccagcgcgg tgctatcgga cagagcctgg cgagcgcaag      60
cggcgcgggg agccagcggg gctgagcgcg ccagggtct  gaacccagat tcccagact     120 agctaccact ccgcttgccc acgccccggg agctcgcggc gcctggcggt cagcgaccag     180
acgtccgggg ccgctgcgct cctggcccgc gaggcgtgac actgtctcgg ctacagaccc     240
agagggagca cactgccagg atg gga gct gct ggg agg cag gac ttc ctc ttc     293
                      Met Gly Ala Ala Gly Arg Gln Asp Phe Leu Phe
                        1               5                  10 aag gcc atg ctg acc atc agc tgg ctc act ctg acc tgc ttc cct ggg       341
Lys Ala Met Leu Thr Ile Ser Trp Leu Thr Leu Thr Cys Phe Pro Gly
             15                  20                  25 gcc aca tcc aca gtg gct gct ggg tgc cct gac cag agc cct gag ttg       389
Ala Thr Ser Thr Val Ala Ala Gly Cys Pro Asp Gln Ser Pro Glu Leu
         30                  35                  40 caa ccc tgg aac cct ggc cat gac caa gac cac cat gtg cat atc ggc       437
Gln Pro Trp Asn Pro Gly His Asp Gln Asp His His Val His Ile Gly
     45                  50                  55 cag ggc aag aca ctg ctg ctc acc tct tct gcc acg gtc tat tcc atc       485
Gln Gly Lys Thr Leu Leu Leu Thr Ser Ser Ala Thr Val Tyr Ser Ile
 60                  65                  70                  75 cac atc tca gag gga ggc aag ctg gtc att aaa gac cac gac gag ccg       533
His Ile Ser Glu Gly Gly Lys Leu Val Ile Lys Asp His Asp Glu Pro
                 80                  85                  90 att gtt ttg cga acc cgg cac atc ctg att gac aac gga gga gag ctg       581
Ile Val Leu Arg Thr Arg His Ile Leu Ile Asp Asn Gly Gly Glu Leu
             95                 100                 105 cat gct ggg agt gcc ctc tgc cct ttc cag ggc aat ttc acc atc att       629
His Ala Gly Ser Ala Leu Cys Pro Phe Gln Gly Asn Phe Thr Ile Ile
        110                 115                 120 ttg tat gga agg gct gat gaa ggt att cag ccg gat cct tac tat ggt       677
Leu Tyr Gly Arg Ala Asp Glu Gly Ile Gln Pro Asp Pro Tyr Tyr Gly
    125                 130                 135 ctg aag tac att ggg gtt ggt aaa gga ggc gct ctt gag ttg cat gga       725
Leu Lys Tyr Ile Gly Val Gly Lys Gly Gly Ala Leu Glu Leu His Gly
140                 145                 150                 155 cag aaa aag ctc tcc tgg aca ttt ctg aac aag acc ctt cac cca ggt       773
Gln Lys Lys Leu Ser Trp Thr Phe Leu Asn Lys Thr Leu His Pro Gly
                160                 165                 170 ggc atg gca gaa gga ggc tat ttt ttt gaa agg agc tgg ggc cac cgt       821
Gly Met Ala Glu Gly Gly Tyr Phe Phe Glu Arg Ser Trp Gly His Arg
            175                 180                 185 gga gtt att gtt cat gtc atc gac ccc aaa tca ggc aca gtc atc cat       869
```

```
                Gly Val Ile Val His Val Ile Asp Pro Lys Ser Gly Thr Val Ile His
                            190                 195                 200 tct gac cgg ttt gac acc tat aga tcc aag aaa gag agt gaa cgt ctg         917
Ser Asp Arg Phe Asp Thr Tyr Arg Ser Lys Lys Glu Ser Glu Arg Leu
205                 210                 215 gtc cag tat ttg aac gcg gtg ccc gat ggc agg atc ctt tct gtt gca         965
Val Gln Tyr Leu Asn Ala Val Pro Asp Gly Arg Ile Leu Ser Val Ala
220                 225                 230                 235 gtg aat gat gaa ggt tct cga aat ctg gat gac atg gcc agg aag gcg        1013
Val Asn Asp Glu Gly Ser Arg Asn Leu Asp Asp Met Ala Arg Lys Ala
                240                 245                 250 atg acc aaa ttg gga agc aaa cac ttc ctg cac ctt gga ttt aga cac        1061
Met Thr Lys Leu Gly Ser Lys His Phe Leu His Leu Gly Phe Arg His
                255                 260                 265 cct tgg agt ttt cta act gtg aaa gga aat cca tca tct tca gtg gaa        1109
Pro Trp Ser Phe Leu Thr Val Lys Gly Asn Pro Ser Ser Ser Val Glu
                270                 275                 280 gac cat att gaa tat cat gga cat cga ggc tct gct gct gcc cgg gta        1157
Asp His Ile Glu Tyr His Gly His Arg Gly Ser Ala Ala Ala Arg Val
285                 290                 295 ttc aaa ttg ttc cag aca gag cat ggc gaa tat ttc aat gtt tct ttg        1205
Phe Lys Leu Phe Gln Thr Glu His Gly Glu Tyr Phe Asn Val Ser Leu
300                 305                 310                 315 tcc agt gag tgg gtt caa gac gtg gag tgg acg gag tgg ttc gat cat        1253
Ser Ser Glu Trp Val Gln Asp Val Glu Trp Thr Glu Trp Phe Asp His
                320                 325                 330 gat aaa gta tct cag act aaa ggt ggg gag aaa att tca gac ctc tgg        1301
Asp Lys Val Ser Gln Thr Lys Gly Gly Glu Lys Ile Ser Asp Leu Trp
                335                 340                 345 aaa gct cac cca gga aaa ata tgc aat cgt ccc att gat ata cag gcc        1349
Lys Ala His Pro Gly Lys Ile Cys Asn Arg Pro Ile Asp Ile Gln Ala
                350                 355                 360 act aca atg gat gga gtt aac ctc agc acc gag gtt gtc tac aaa aaa        1397
Thr Thr Met Asp Gly Val Asn Leu Ser Thr Glu Val Val Tyr Lys Lys
365                 370                 375 ggc cag gat tat agg ttt gct tgc tac gac cgg ggc aga gcc tgc cgg        1445
Gly Gln Asp Tyr Arg Phe Ala Cys Tyr Asp Arg Gly Arg Ala Cys Arg
380                 385                 390                 395 agc tac cgt gta cgg ttc ctc tgt ggg aag cct gtg agg ccc aaa ctc        1493
Ser Tyr Arg Val Arg Phe Leu Cys Gly Lys Pro Val Arg Pro Lys Leu
                400                 405                 410 aca gtc acc att gac acc aat gtg aac agc acc att ctg aac ttg gag        1541
Thr Val Thr Ile Asp Thr Asn Val Asn Ser Thr Ile Leu Asn Leu Glu
                415                 420                 425 gat aat gta cag tca tgg aaa cct gga gat acc ctg gtc att gcc agt        1589
Asp Asn Val Gln Ser Trp Lys Pro Gly Asp Thr Leu Val Ile Ala Ser
                430                 435                 440 act gat tac tcc atg tac cag gca gaa gag ttc cag gtg ctt ccc tgc        1637
Thr Asp Tyr Ser Met Tyr Gln Ala Glu Glu Phe Gln Val Leu Pro Cys
445                 450                 455 aga tcc tgc gcc ccc aac cag gtc aaa gtg gca ggg aaa cca atg tac        1685
Arg Ser Cys Ala Pro Asn Gln Val Lys Val Ala Gly Lys Pro Met Tyr
460                 465                 470                 475 ctg cac atc ggg gag gag ata gac ggc gtg gac atg cgg gcg gag gtt        1733
Leu His Ile Gly Glu Glu Ile Asp Gly Val Asp Met Arg Ala Glu Val
                480                 485                 490 ggg ctt ctg agc cgg aac atc ata gtg atg ggg gag atg gag gac aaa        1781
Gly Leu Leu Ser Arg Asn Ile Ile Val Met Gly Glu Met Glu Asp Lys
                495                 500                 505
```

```
tgc tac ccc tac aga aac cac atc tgc aat ttc ttt gac ttc gat acc    1829
Cys Tyr Pro Tyr Arg Asn His Ile Cys Asn Phe Phe Asp Phe Asp Thr
        510             515                 520 ttt ggg ggc cac atc aag ttt gct ctg gga ttt aag gca gca cac ttg    1877
Phe Gly Gly His Ile Lys Phe Ala Leu Gly Phe Lys Ala Ala His Leu
        525             530                 535 gag ggc acg gag ctg aag cat atg gga cag cag ctg gtg ggt cag tac    1925
Glu Gly Thr Glu Leu Lys His Met Gly Gln Gln Leu Val Gly Gln Tyr
540             545                 550                 555 ccg att cac ttc cac ctg gcc ggt gat gta gac gaa agg gga ggt tat    1973
Pro Ile His Phe His Leu Ala Gly Asp Val Asp Glu Arg Gly Gly Tyr
            560                 565                 570 gac cca ccc aca tac atc agg gac ctc tcc atc cat cat aca ttc tct    2021
Asp Pro Pro Thr Tyr Ile Arg Asp Leu Ser Ile His His Thr Phe Ser
                575                 580                 585 cgc tgc gtc aca gtc cat ggc tcc aat ggc ttg ttg atc aag gac gtt    2069
Arg Cys Val Thr Val His Gly Ser Asn Gly Leu Leu Ile Lys Asp Val
                    590                 595                 600 gtg ggc tat aac tct ttg ggc cac tgc ttc ttc acg gaa gat ggg ccg    2117
Val Gly Tyr Asn Ser Leu Gly His Cys Phe Phe Thr Glu Asp Gly Pro
605             610                 615 gag gaa cgc aac act ttt gac cac tgt ctt ggc ctc ctt gtc aag tct    2165
Glu Glu Arg Asn Thr Phe Asp His Cys Leu Gly Leu Leu Val Lys Ser
620             625                 630                 635 gga acc ctc ctc ccc tcg gac cgt gac agc aag atg tgc aag atg atc    2213
Gly Thr Leu Leu Pro Ser Asp Arg Asp Ser Lys Met Cys Lys Met Ile
            640                 645                 650 aca gag gac tcc tac ccg ggg tac atc ccc aag ccc agg caa gac tgc    2261
Thr Glu Asp Ser Tyr Pro Gly Tyr Ile Pro Lys Pro Arg Gln Asp Cys
                655                 660                 665 aat gct gtg tcc acc ttc tgg atg gcc aat ccc aac aac aac ctc atc    2309
Asn Ala Val Ser Thr Phe Trp Met Ala Asn Pro Asn Asn Asn Leu Ile
                    670                 675                 680 aac tgt gcc gct gca gga tct gag gaa act gga ttt tgg ttt att ttt    2357
Asn Cys Ala Ala Ala Gly Ser Glu Glu Thr Gly Phe Trp Phe Ile Phe
685             690                 695 cac cac gta cca acg ggc ccc tcc gtg gga atg tac tcc cca ggt tat    2405
His His Val Pro Thr Gly Pro Ser Val Gly Met Tyr Ser Pro Gly Tyr
700             705                 710                 715 tca gag cac att cca ctg gga aaa ttc tat aac aac cga gca cat tcc    2453
Ser Glu His Ile Pro Leu Gly Lys Phe Tyr Asn Asn Arg Ala His Ser
            720                 725                 730 aac tac cgg gct ggc atg atc ata gac aac gga gtc aaa acc acc gag    2501
Asn Tyr Arg Ala Gly Met Ile Ile Asp Asn Gly Val Lys Thr Thr Glu
                735                 740                 745 gcc tct gcc aag gac aag cgg ccg ttc ctc tca atc atc tct gcc aga    2549
Ala Ser Ala Lys Asp Lys Arg Pro Phe Leu Ser Ile Ile Ser Ala Arg
                    750                 755                 760 tac agc cct cac cag gac gcc gac ccg ctg aag ccc cgg gag ccg gcc    2597
Tyr Ser Pro His Gln Asp Ala Asp Pro Leu Lys Pro Arg Glu Pro Ala
765             770                 775 atc atc aga cac ttc att gcc tac aag aac cag gac cac ggg gcc tgg    2645
Ile Ile Arg His Phe Ile Ala Tyr Lys Asn Gln Asp His Gly Ala Trp
780             785                 790                 795 ctg cgc ggc ggg gat gtg tgg ctg gac agc tgc cgg ttt gct gac aat    2693
Leu Arg Gly Gly Asp Val Trp Leu Asp Ser Cys Arg Phe Ala Asp Asn
            800                 805                 810 ggc att ggc ctg acc ctg gcc agt ggt gga acc ttc ccg tat gac gac    2741
Gly Ile Gly Leu Thr Leu Ala Ser Gly Gly Thr Phe Pro Tyr Asp Asp
                815                 820                 825
```

```
ggc tcc aag caa gag ata aag aac agc ttg ttt gtt ggc gag agt ggc      2789
Gly Ser Lys Gln Glu Ile Lys Asn Ser Leu Phe Val Gly Glu Ser Gly
        830                 835                 840 aac gtg ggg acg gaa atg atg gac aat agg atc tgg ggc cct ggc ggc      2837
Asn Val Gly Thr Glu Met Met Asp Asn Arg Ile Trp Gly Pro Gly Gly
845                 850                 855 ttg gac cat agc gga agg acc ctc cct ata ggc cag aat ttt cca att      2885
Leu Asp His Ser Gly Arg Thr Leu Pro Ile Gly Gln Asn Phe Pro Ile
860                 865                 870                 875 aga gga att cag tta tat gat ggc ccc atc aac atc caa aac tgc act      2933
Arg Gly Ile Gln Leu Tyr Asp Gly Pro Ile Asn Ile Gln Asn Cys Thr
            880                 885                 890 ttc cga aag ttt gtg gcc ctg gag ggc cgg cac acc agc gcc ctg gcc      2981
Phe Arg Lys Phe Val Ala Leu Glu Gly Arg His Thr Ser Ala Leu Ala
            895                 900                 905 ttc cgc ctg aat aat gcc tgg cag agc tgc ccc cat aac aac gtg acc      3029
Phe Arg Leu Asn Asn Ala Trp Gln Ser Cys Pro His Asn Asn Val Thr
            910                 915                 920 ggc att gcc ttt gag gac gtt ccg att act tcc aga gtg ttc ttc gga      3077
Gly Ile Ala Phe Glu Asp Val Pro Ile Thr Ser Arg Val Phe Phe Gly
925                 930                 935 gag cct ggg ccc tgg ttc aac cag ctg gac atg gat ggg gat aag aca      3125
Glu Pro Gly Pro Trp Phe Asn Gln Leu Asp Met Asp Gly Asp Lys Thr
940                 945                 950                 955 tct gtg ttc cat gac gtc gac ggc tcc gtg tcc gag tac cct ggc tcc      3173
Ser Val Phe His Asp Val Asp Gly Ser Val Ser Glu Tyr Pro Gly Ser
            960                 965                 970 tac ctc acg aag aat gac aac tgg ctg gtc cgg cac cca gac tgc atc      3221
Tyr Leu Thr Lys Asn Asp Asn Trp Leu Val Arg His Pro Asp Cys Ile
            975                 980                 985 aat gtt ccc gac tgg aga ggg gcc att tgc agt ggg tgc tat gca cag      3269
Asn Val Pro Asp Trp Arg Gly Ala Ile Cys Ser Gly Cys Tyr Ala Gln
990                 995                 1000 atg tac att caa gcc tac aag acc agt aac ctg cga atg aag atc       3314
Met Tyr Ile Gln Ala Tyr Lys Thr Ser Asn Leu Arg Met Lys Ile
    1005                1010                1015 atc aag aat gac ttc ccc agc cac cct ctt tac ctg gag ggg gcg       3359
Ile Lys Asn Asp Phe Pro Ser His Pro Leu Tyr Leu Glu Gly Ala
1020                1025                1030 ctc acc agg agc acc cat tac cag caa tac caa ccg gtt gtc acc       3404
Leu Thr Arg Ser Thr His Tyr Gln Gln Tyr Gln Pro Val Val Thr
1035                1040                1045 ctg cag aag ggc tac acc atc cac tgg gac cag acg gcc ccc gcc       3449
Leu Gln Lys Gly Tyr Thr Ile His Trp Asp Gln Thr Ala Pro Ala
1050                1055                1060 gaa ctc gcc atc tgg ctc atc aac ttc aac aag ggc gac tgg atc       3494
Glu Leu Ala Ile Trp Leu Ile Asn Phe Asn Lys Gly Asp Trp Ile
1065                1070                1075 cga gtg ggg ctc tgc tac ccg cga ggc acc aca ttc tcc atc ctc       3539
Arg Val Gly Leu Cys Tyr Pro Arg Gly Thr Thr Phe Ser Ile Leu
    1080                1085                1090 tcg gat gtt cac aat cgc ctg ctg aag caa acg tcc aag acg ggc       3584
Ser Asp Val His Asn Arg Leu Leu Lys Gln Thr Ser Lys Thr Gly
1095                1100                1105 gtc ttc gtg agg acc ttg cag atg gac aaa gtg gag cag agc tac       3629
Val Phe Val Arg Thr Leu Gln Met Asp Lys Val Glu Gln Ser Tyr
1110                1115                1120 cct ggc agg agc cac tac tac tgg gac gag gac tca ggg ctg ttg       3674
Pro Gly Arg Ser His Tyr Tyr Trp Asp Glu Asp Ser Gly Leu Leu
```

-continued

|  |  |  |  |  |  |  |  |  |  |  |  |  |
|---|---|---|---|---|---|---|---|---|---|---|---|---|
| | 1125 | | | 1130 | | | | 1135 | | | | |
| ttc | ctg | aag | ctg | aaa | gct | cag | aac | gag | aga | gag | aag | ttt gct ttc | 3719 |
| Phe | Leu | Lys | Leu | Lys | Ala | Gln | Asn | Glu | Arg | Glu | Lys | Phe Ala Phe |
| | 1140 | | | | 1145 | | | | 1150 | | | |
| tgc | tcc | atg | aaa | ggc | tgt | gag | agg | ata | aag | att | aaa | gct ctg att | 3764 |
| Cys | Ser | Met | Lys | Gly | Cys | Glu | Arg | Ile | Lys | Ile | Lys | Ala Leu Ile |
| | 1155 | | | | 1160 | | | | 1165 | | | |
| cca | aag | aac | gca | ggc | gtc | agt | gac | tgc | aca | gcc | aca | gct tac ccc | 3809 |
| Pro | Lys | Asn | Ala | Gly | Val | Ser | Asp | Cys | Thr | Ala | Thr | Ala Tyr Pro |
| | 1170 | | | | 1175 | | | | 1180 | | | |
| aag | ttc | acc | gag | agg | gct | gtc | gta | gac | gtg | ccg | atg | ccc aag aag | 3854 |
| Lys | Phe | Thr | Glu | Arg | Ala | Val | Val | Asp | Val | Pro | Met | Pro Lys Lys |
| | 1185 | | | | 1190 | | | | 1195 | | | |
| ctc | ttt | ggt | tct | cag | ctg | aaa | aca | aag | gac | cat | ttc | ttg gag gtg | 3899 |
| Leu | Phe | Gly | Ser | Gln | Leu | Lys | Thr | Lys | Asp | His | Phe | Leu Glu Val |
| | 1200 | | | | 1205 | | | | 1210 | | | |
| aag | atg | gag | agt | tcc | aag | cag | cac | ttc | ttc | cac | ctc | tgg aac gac | 3944 |
| Lys | Met | Glu | Ser | Ser | Lys | Gln | His | Phe | Phe | His | Leu | Trp Asn Asp |
| | 1215 | | | | 1220 | | | | 1225 | | | |
| ttc | gct | tac | att | gaa | gtg | gat | ggg | aag | aag | tac | ccc | agt tcg gag | 3989 |
| Phe | Ala | Tyr | Ile | Glu | Val | Asp | Gly | Lys | Lys | Tyr | Pro | Ser Ser Glu |
| | 1230 | | | | 1235 | | | | 1240 | | | |
| gat | ggc | atc | cag | gtg | gtg | gtg | att | gac | ggg | aac | caa | ggg cgc gtg | 4034 |
| Asp | Gly | Ile | Gln | Val | Val | Val | Ile | Asp | Gly | Asn | Gln | Gly Arg Val |
| | 1245 | | | | 1250 | | | | 1255 | | | |
| gtg | agc | cac | acg | agc | ttc | agg | aac | tcc | att | ctg | caa | ggc ata cca | 4079 |
| Val | Ser | His | Thr | Ser | Phe | Arg | Asn | Ser | Ile | Leu | Gln | Gly Ile Pro |
| | 1260 | | | | 1265 | | | | 1270 | | | |
| tgg | cag | ctt | ttc | aac | tat | gtg | gcg | acc | atc | cct | gac | aat tcc ata | 4124 |
| Trp | Gln | Leu | Phe | Asn | Tyr | Val | Ala | Thr | Ile | Pro | Asp | Asn Ser Ile |
| | 1275 | | | | 1280 | | | | 1285 | | | |
| gtg | ctt | atg | gca | tca | aag | gga | aga | tac | gtc | tcc | aga | ggc cca tgg | 4169 |
| Val | Leu | Met | Ala | Ser | Lys | Gly | Arg | Tyr | Val | Ser | Arg | Gly Pro Trp |
| | 1290 | | | | 1295 | | | | 1300 | | | |
| acc | aga | gtg | ctg | gaa | aag | ctt | ggg | gca | gac | agg | ggt | ctc aag ttg | 4214 |
| Thr | Arg | Val | Leu | Glu | Lys | Leu | Gly | Ala | Asp | Arg | Gly | Leu Lys Leu |
| | 1305 | | | | 1310 | | | | 1315 | | | |
| aaa | gag | caa | atg | gca | ttc | gtt | ggc | ttc | aaa | ggc | agc | ttc cgg ccc | 4259 |
| Lys | Glu | Gln | Met | Ala | Phe | Val | Gly | Phe | Lys | Gly | Ser | Phe Arg Pro |
| | 1320 | | | | 1325 | | | | 1330 | | | |
| atc | tgg | gtg | aca | ctg | gac | act | gag | gat | cac | aaa | gcc | aaa atc ttc | 4304 |
| Ile | Trp | Val | Thr | Leu | Asp | Thr | Glu | Asp | His | Lys | Ala | Lys Ile Phe |
| | 1335 | | | | 1340 | | | | 1345 | | | |
| caa | gtt | gtg | ccc | atc | cct | gtg | gtg | aag | aag | aag | aag | ttg tga | 4346 |
| Gln | Val | Val | Pro | Ile | Pro | Val | Val | Lys | Lys | Lys | Lys | Leu |
| | 1350 | | | | 1355 | | | | 1360 | | | | ggacagctgc cgcccggtgc cacctcgtgg tagactatga cggtgactct tggcagcaga     4406 ccagtggggg atggctgggt cccccagccc ctgccagcag ctgcctggga aggccgtgtt     4466 tcagccctga tgggccaagg gaaggctatc agagaccctg gtgctgccac ctgccctac      4526 tcaagtgtct acctggagcc cctggggcgg tgctggccaa tgctggaaac attcactttc     4586 ctgcagcctc ttgggtgctt ctctcctatc tgtgcctctt cagtgggggt ttggggacca     4646 tatcaggaga cctgggttgt gctgacagca agatccact ttggcaggag ccctgaccca     4706 gctaggaggt agtctggagg gctggtcatt cacagatccc catggtcttc agcagacaag     4766 tgagggtggt aaatgtagga gaaagagcct tggcctaag gaaatcttta ctcctgtaag      4826 caagagccaa cctcacagga ttaggagctg ggtagaact ggctatcctt ggggaagagg      4886

```
caagccctgc ctctggccgt gtccaccttt caggagactt tgagtggcag gtttggactt    4946
ggactagatg actctcaaag gcccttttag ttctgagatt ccagaaatct gctgcatttc    5006
acatggtacc tggaacccaa cagttcatgg atatccactg atatccatga tgctgggtgc    5066
cccagcgcac acgggatgga gaggtgagaa ctaatgccta gcttgagggg tctgcagtcc    5126
agtagggcag gcagtcaggt ccatgtgcac tgcaatgcca ggtggagaaa tcacagagag    5186
gtaaaatgga ggccagtgcc atttcagagg ggaggctcag gaaggcttct tgcttacagg    5246
aatgaaggct gggggcattt tgctgggggg agatgaggca gcctctggaa tggctcaggg    5306
attcagccct ccctgccgct gcctgctgaa gctggtgact acggggtcgc cctttgctca    5366
cgtctctctg gcccactcat gatggagaag tgtggtcaga ggggagcaat gggctttgct    5426
gcttatgagc acagaggaat tcagtcccca ggcagccctg cctctgactc caagagggtg    5486
aagtccacag aagtgagctc ctgccttagg gcctcatttg ctcttcatcc agggaactga    5546
gcacaggggg cctccaggag acctagatg tgctcgtact ccctcggcct gggatttcag    5606
agctggaaat atagaaaata tctagcccaa agccttcatt ttaacagatg gggaaagtga    5666
gcccccaaga tgggaaagaa ccacacagct aagggagggc ctggggagcc ccaccctagc    5726
ccttgctgcc acaccacatt gcctcaacaa ccggcccag agtgcccagg cactcctgag    5786
gtagcttctg gaaatgggga caagtcccct cgaaggaaag gaaatgacta gagtagaatg    5846
acagctagca gatctcttcc ctcctgctcc cagcgcacac aaacccgccc tccccttggt    5906
gttggcggtc cctgtggcct tcactttgtt cactacctgt cagcccagcc tgggtgcaca    5966
gtagctgcaa ctccccattg gtgctacctg gctctcctgt ctctgcagct ctacaggtga    6026
ggcccagcag agggagtagg gctcgccatg tttctggtga gccaatttgg ctgatcttgg    6086
gtgtctgaac agctattggg tccacccag tcccttcag ctgctgctta atgccctgct    6146
ctctccctgg cccaccttat agagagccca aagagctcct gtaagaggga gaactctatc    6206
tgtggtttat aatcttgcac gaggcaccag agtctccctg ggtcttgtga tgaactacat    6266
ttatcccctt tcctgcccca accacaaact ctttccttca aagagggcct gcctggctcc    6326
ctccacccaa ctgcacccat gagactcggt ccaagagtcc attccccagg tgggagccaa    6386
ctgtcaggga ggtctttccc accaaacatc tttcagctgc tgggaggtga ccatagggct    6446
ctgcttttaa agatatggct gcttcaaagg ccagagtcac aggaaggact tcttccaggg    6506
agattagtgg tgatggagag gagagttaaa atgacctcat gtccttcttg tccacggttt    6566
tgttgagttt tcactcttct aatgcaaggg tctcacactg tgaaccactt aggatgtgat    6626
cactttcagg tggccaggaa tgttgaatgt ctttggctca gttcatttaa aaaagatatc    6686
tatttgaaag ttctcagagt tgtacatatg tttcacagta caggatctgt acataaaagt    6746
ttctttccta aaccattcac caagagccaa tatctaggca ttttcttggt agcacaaatt    6806
ttcttattgc ttagaaaatt gtcctccttg ttatttctgt ttgtaagact taagtgagtt    6866
aggtctttaa ggaaagcaac gctcctctga aatgcttgtc ttttttctgt tgccgaaata    6926
gctggtcctt tttcgggagt tagatgtata gagtgtttgt atgtaaacat ttcttgtagg    6986
catcaccatg aacaaagata tattttctat ttatttatta tatgtgcact tcaagaagtc    7046
actgtcagag aaataaagaa ttgtcttaaa tgtc                                7080
```

<210> SEQ ID NO 2
<211> LENGTH: 1361
<212> TYPE: PRT

-continued

<213> ORGANISM: Homo sapiens

<400> SEQUENCE: 2

Met Gly Ala Ala Gly Arg Gln Asp Phe Leu Phe Lys Ala Met Leu Thr
 1               5                  10                  15

Ile Ser Trp Leu Thr Leu Thr Cys Phe Pro Gly Ala Thr Ser Thr Val
            20                  25                  30

Ala Ala Gly Cys Pro Asp Gln Ser Pro Glu Leu Gln Pro Trp Asn Pro
        35                  40                  45

Gly His Asp Gln Asp His His Val His Ile Gly Gln Gly Lys Thr Leu
    50                  55                  60

Leu Leu Thr Ser Ser Ala Thr Val Tyr Ser Ile His Ile Ser Glu Gly
65                  70                  75                  80

Gly Lys Leu Val Ile Lys Asp His Asp Glu Pro Ile Val Leu Arg Thr
                85                  90                  95

Arg His Ile Leu Ile Asp Asn Gly Gly Glu Leu His Ala Gly Ser Ala
            100                 105                 110

Leu Cys Pro Phe Gln Gly Asn Phe Thr Ile Ile Leu Tyr Gly Arg Ala
        115                 120                 125

Asp Glu Gly Ile Gln Pro Asp Pro Tyr Tyr Gly Leu Lys Tyr Ile Gly
    130                 135                 140

Val Gly Lys Gly Gly Ala Leu Glu Leu His Gly Gln Lys Lys Leu Ser
145                 150                 155                 160

Trp Thr Phe Leu Asn Lys Thr Leu His Pro Gly Gly Met Ala Glu Gly
                165                 170                 175

Gly Tyr Phe Phe Glu Arg Ser Trp Gly His Arg Gly Val Ile Val His
            180                 185                 190

Val Ile Asp Pro Lys Ser Gly Thr Val Ile His Ser Asp Arg Phe Asp
        195                 200                 205

Thr Tyr Arg Ser Lys Lys Glu Ser Glu Arg Leu Val Gln Tyr Leu Asn
    210                 215                 220

Ala Val Pro Asp Gly Arg Ile Leu Ser Val Ala Val Asn Asp Glu Gly
225                 230                 235                 240

Ser Arg Asn Leu Asp Asp Met Ala Arg Lys Ala Met Thr Lys Leu Gly
                245                 250                 255

Ser Lys His Phe Leu His Leu Gly Phe Arg His Pro Trp Ser Phe Leu
            260                 265                 270

Thr Val Lys Gly Asn Pro Ser Ser Ser Val Glu Asp His Ile Glu Tyr
        275                 280                 285

His Gly His Arg Gly Ser Ala Ala Arg Val Phe Lys Leu Phe Gln
    290                 295                 300

Thr Glu His Gly Glu Tyr Phe Asn Val Ser Leu Ser Ser Glu Trp Val
305                 310                 315                 320

Gln Asp Val Glu Trp Thr Glu Trp Phe Asp His Asp Lys Val Ser Gln
                325                 330                 335

Thr Lys Gly Gly Glu Lys Ile Ser Asp Leu Trp Lys Ala His Pro Gly
            340                 345                 350

Lys Ile Cys Asn Arg Pro Ile Asp Ile Gln Ala Thr Thr Met Asp Gly
        355                 360                 365

Val Asn Leu Ser Thr Glu Val Val Tyr Lys Lys Gly Gln Asp Tyr Arg
    370                 375                 380

Phe Ala Cys Tyr Asp Arg Gly Arg Ala Cys Arg Ser Tyr Arg Val Arg
385                 390                 395                 400

-continued

```
Phe Leu Cys Gly Lys Pro Val Arg Pro Lys Leu Thr Val Thr Ile Asp
            405                 410                 415
Thr Asn Val Asn Ser Thr Ile Leu Asn Leu Glu Asp Asn Val Gln Ser
        420                 425                 430
Trp Lys Pro Gly Asp Thr Leu Val Ile Ala Ser Thr Asp Tyr Ser Met
    435                 440                 445
Tyr Gln Ala Glu Glu Phe Gln Val Leu Pro Cys Arg Ser Cys Ala Pro
450                 455                 460
Asn Gln Val Lys Val Ala Gly Lys Pro Met Tyr Leu His Ile Gly Glu
465                 470                 475                 480
Glu Ile Asp Gly Val Asp Met Arg Ala Glu Val Gly Leu Leu Ser Arg
                485                 490                 495
Asn Ile Ile Val Met Gly Glu Met Glu Asp Lys Cys Tyr Pro Tyr Arg
            500                 505                 510
Asn His Ile Cys Asn Phe Phe Asp Phe Asp Thr Phe Gly Gly His Ile
        515                 520                 525
Lys Phe Ala Leu Gly Phe Lys Ala Ala His Leu Glu Gly Thr Glu Leu
    530                 535                 540
Lys His Met Gly Gln Gln Leu Val Gly Gln Tyr Pro Ile His Phe His
545                 550                 555                 560
Leu Ala Gly Asp Val Asp Glu Arg Gly Gly Tyr Asp Pro Pro Thr Tyr
                565                 570                 575
Ile Arg Asp Leu Ser Ile His His Thr Phe Ser Arg Cys Val Thr Val
            580                 585                 590
His Gly Ser Asn Gly Leu Leu Ile Lys Asp Val Val Gly Tyr Asn Ser
        595                 600                 605
Leu Gly His Cys Phe Phe Thr Glu Asp Gly Pro Glu Glu Arg Asn Thr
    610                 615                 620
Phe Asp His Cys Leu Gly Leu Leu Val Lys Ser Gly Thr Leu Leu Pro
625                 630                 635                 640
Ser Asp Arg Asp Ser Lys Met Cys Lys Met Ile Thr Glu Asp Ser Tyr
                645                 650                 655
Pro Gly Tyr Ile Pro Lys Pro Arg Gln Asp Cys Asn Ala Val Ser Thr
            660                 665                 670
Phe Trp Met Ala Asn Pro Asn Asn Leu Ile Asn Cys Ala Ala Ala
        675                 680                 685
Gly Ser Glu Glu Thr Gly Phe Trp Phe Ile Phe His His Val Pro Thr
    690                 695                 700
Gly Pro Ser Val Gly Met Tyr Ser Pro Gly Tyr Ser Glu His Ile Pro
705                 710                 715                 720
Leu Gly Lys Phe Tyr Asn Asn Arg Ala His Ser Asn Tyr Arg Ala Gly
                725                 730                 735
Met Ile Ile Asp Asn Gly Val Lys Thr Thr Glu Ala Ser Ala Lys Asp
            740                 745                 750
Lys Arg Pro Phe Leu Ser Ile Ile Ser Ala Arg Tyr Ser Pro His Gln
        755                 760                 765
Asp Ala Asp Pro Leu Lys Pro Arg Glu Pro Ala Ile Ile Arg His Phe
    770                 775                 780
Ile Ala Tyr Lys Asn Gln Asp His Gly Ala Trp Leu Arg Gly Gly Asp
785                 790                 795                 800
Val Trp Leu Asp Ser Cys Arg Phe Ala Asp Asn Gly Ile Gly Leu Thr
                805                 810                 815
Leu Ala Ser Gly Gly Thr Phe Pro Tyr Asp Asp Gly Ser Lys Gln Glu
```

```
            820             825             830
Ile Lys Asn Ser Leu Phe Val Gly Glu Ser Gly Asn Val Gly Thr Glu
        835             840             845
Met Met Asp Asn Arg Ile Trp Gly Pro Gly Gly Leu Asp His Ser Gly
850             855             860
Arg Thr Leu Pro Ile Gly Gln Asn Phe Pro Ile Arg Gly Ile Gln Leu
865             870             875             880
Tyr Asp Gly Pro Ile Asn Ile Gln Asn Cys Thr Phe Arg Lys Phe Val
            885             890             895
Ala Leu Glu Gly Arg His Thr Ser Ala Leu Ala Phe Arg Leu Asn Asn
        900             905             910
Ala Trp Gln Ser Cys Pro His Asn Asn Val Thr Gly Ile Ala Phe Glu
    915             920             925
Asp Val Pro Ile Thr Ser Arg Val Phe Gly Glu Pro Gly Pro Trp
930             935             940
Phe Asn Gln Leu Asp Met Asp Gly Asp Lys Thr Ser Val Phe His Asp
945             950             955             960
Val Asp Gly Ser Val Ser Glu Tyr Pro Gly Ser Tyr Leu Thr Lys Asn
            965             970             975
Asp Asn Trp Leu Val Arg His Pro Asp Cys Ile Asn Val Pro Asp Trp
        980             985             990
Arg Gly Ala Ile Cys Ser Gly Cys Tyr Ala Gln Met Tyr Ile Gln Ala
        995             1000            1005
Tyr Lys Thr Ser Asn Leu Arg Met Lys Ile Ile Lys Asn Asp Phe
    1010            1015            1020
Pro Ser His Pro Leu Tyr Leu Glu Gly Ala Leu Thr Arg Ser Thr
    1025            1030            1035
His Tyr Gln Gln Tyr Gln Pro Val Val Thr Leu Gln Lys Gly Tyr
    1040            1045            1050
Thr Ile His Trp Asp Gln Thr Ala Pro Ala Glu Leu Ala Ile Trp
    1055            1060            1065
Leu Ile Asn Phe Asn Lys Gly Asp Trp Ile Arg Val Gly Leu Cys
    1070            1075            1080
Tyr Pro Arg Gly Thr Thr Phe Ser Ile Leu Ser Asp Val His Asn
    1085            1090            1095
Arg Leu Leu Lys Gln Thr Ser Lys Thr Gly Val Phe Val Arg Thr
    1100            1105            1110
Leu Gln Met Asp Lys Val Glu Gln Ser Tyr Pro Gly Arg Ser His
    1115            1120            1125
Tyr Tyr Trp Asp Glu Asp Ser Gly Leu Leu Phe Leu Lys Leu Lys
    1130            1135            1140
Ala Gln Asn Glu Arg Glu Lys Phe Ala Phe Cys Ser Met Lys Gly
    1145            1150            1155
Cys Glu Arg Ile Lys Ile Lys Ala Leu Ile Pro Lys Asn Ala Gly
    1160            1165            1170
Val Ser Asp Cys Thr Ala Thr Ala Tyr Pro Lys Phe Thr Glu Arg
    1175            1180            1185
Ala Val Val Asp Val Pro Met Pro Lys Lys Leu Phe Gly Ser Gln
    1190            1195            1200
Leu Lys Thr Lys Asp His Phe Leu Glu Val Lys Met Glu Ser Ser
    1205            1210            1215
Lys Gln His Phe Phe His Leu Trp Asn Asp Phe Ala Tyr Ile Glu
    1220            1225            1230
```

```
Val Asp Gly Lys Lys Tyr Pro Ser Ser Glu Asp Gly Ile Gln Val
    1235                1240                1245

Val Val Ile Asp Gly Asn Gln Gly Arg Val Val Ser His Thr Ser
    1250                1255                1260

Phe Arg Asn Ser Ile Leu Gln Gly Ile Pro Trp Gln Leu Phe Asn
    1265                1270                1275

Tyr Val Ala Thr Ile Pro Asp Asn Ser Ile Val Leu Met Ala Ser
    1280                1285                1290

Lys Gly Arg Tyr Val Ser Arg Gly Pro Trp Thr Arg Val Leu Glu
    1295                1300                1305

Lys Leu Gly Ala Asp Arg Gly Leu Lys Leu Lys Glu Gln Met Ala
    1310                1315                1320

Phe Val Gly Phe Lys Gly Ser Phe Arg Pro Ile Trp Val Thr Leu
    1325                1330                1335

Asp Thr Glu Asp His Lys Ala Lys Ile Phe Gln Val Val Pro Ile
    1340                1345                1350

Pro Val Val Lys Lys Lys Leu
    1355                1360

<210> SEQ ID NO 3
<211> LENGTH: 15
<212> TYPE: PRT
<213> ORGANISM: Artificial
<220> FEATURE:
<223> OTHER INFORMATION: epitope peptide(1) of human KIAA1199

<400> SEQUENCE: 3

Cys Asp Arg Phe Asp Thr Tyr Arg Ser Lys Lys Glu Ser Glu Arg
1               5                   10                  15

<210> SEQ ID NO 4
<211> LENGTH: 17
<212> TYPE: PRT
<213> ORGANISM: Artificial
<220> FEATURE:
<223> OTHER INFORMATION: epitope peptide(2) of human KIAA1199

<400> SEQUENCE: 4

Cys Ala Arg Tyr Ser Pro His Gln Asp Ala Asp Pro Leu Lys Pro Arg
1               5                   10                  15

Glu

<210> SEQ ID NO 5
<211> LENGTH: 15
<212> TYPE: PRT
<213> ORGANISM: Artificial
<220> FEATURE:
<223> OTHER INFORMATION: epitope peptide(3) of human KIAA1199

<400> SEQUENCE: 5

Cys Asp Lys Val Glu Gln Ser Tyr Pro Gly Arg Ser His Tyr Tyr
1               5                   10                  15

<210> SEQ ID NO 6
<211> LENGTH: 25
<212> TYPE: RNA
<213> ORGANISM: Artificial
<220> FEATURE:
<223> OTHER INFORMATION: siRNA(1) against human KIAA1199

<400> SEQUENCE: 6
```

```
aaacauugaa auauucgcca ugcuc                                          25

<210> SEQ ID NO 7
<211> LENGTH: 25
<212> TYPE: RNA
<213> ORGANISM: Artificial
<220> FEATURE:
<223> OTHER INFORMATION: siRNA(2) against human KIAA1199

<400> SEQUENCE: 7
uugacaagga ggccaagaca guggu                                          25

<210> SEQ ID NO 8
<211> LENGTH: 25
<212> TYPE: RNA
<213> ORGANISM: Artificial
<220> FEATURE:
<223> OTHER INFORMATION: siRNA(3) against human KIAA1199

<400> SEQUENCE: 8
uucagcuuca ggaacaacag cccug                                          25

<210> SEQ ID NO 9
<211> LENGTH: 20
<212> TYPE: DNA
<213> ORGANISM: Artificial
<220> FEATURE:
<223> OTHER INFORMATION: primer for amplifying human KIAA1199
      (Forward(1), Forward(3))

<400> SEQUENCE: 9
accatcagct ggctcactct                                                20

<210> SEQ ID NO 10
<211> LENGTH: 20
<212> TYPE: DNA
<213> ORGANISM: Artificial
<220> FEATURE:
<223> OTHER INFORMATION: primer for amplifying human KIAA1199
      (Reverse(1))

<400> SEQUENCE: 10
tgtccatgca actcaagagc                                                20

<210> SEQ ID NO 11
<211> LENGTH: 20
<212> TYPE: DNA
<213> ORGANISM: Artificial
<220> FEATURE:
<223> OTHER INFORMATION: primer for amplifying human KIAA1199
      (Forward(2))

<400> SEQUENCE: 11
gtgggttcaa gacgtggagt                                                20

<210> SEQ ID NO 12
<211> LENGTH: 20
<212> TYPE: DNA
<213> ORGANISM: Artificial
<220> FEATURE:
<223> OTHER INFORMATION: primer for amplifying human KIAA1199
      (Reverse(2))

<400> SEQUENCE: 12
tctatctcct ccccgatgtg                                                20
```

```
<210> SEQ ID NO 13
<211> LENGTH: 20
<212> TYPE: DNA
<213> ORGANISM: Artificial
<220> FEATURE:
<223> OTHER INFORMATION: primer for amplifying human KIAA1199
      (Reverse(3))

<400> SEQUENCE: 13
cctcctttac caaccccaat                                                 20

<210> SEQ ID NO 14
<211> LENGTH: 560
<212> TYPE: DNA
<213> ORGANISM: Artificial
<220> FEATURE:
<223> OTHER INFORMATION: probe(1) for detecting human KIAA1199

<400> SEQUENCE: 14
cttctgccac ggtctattcc atccacatct cagagggagg caagctggtc attaaagacc     60
acgacgagcc gattgttttg cgaacccggc acatcctgat tgacaacgga ggagagctgc    120
atgctgggag tgccctctgc cctttccagg gcaatttcac catcattttg tatggaaggg    180
ctgatgaagg tattcagccg gatccttact atggtctgaa gtacattggg gttggtaaag    240
gaggcgctct tgagttgcat ggacagaaaa agctctcctg gacatttctg aacaagaccc    300
ttcacccagg tggcatggca gaaggaggct attttttga aaggagctgg ggccaccgtg     360
gagttattgt tcatgtcatc gaccccaaat caggcacagt catccattct gaccggtttg    420
acacctatag atccaagaaa gagagtgaac gtctggtcca gtatttgaac gcggtgcccg    480
atggcaggat cctttctgtt gcagtgaatg atgaaggttc tcgaaatctg atgacatgg     540 ccaggaaggc gatgaccaaa                                                560

<210> SEQ ID NO 15
<211> LENGTH: 393
<212> TYPE: DNA
<213> ORGANISM: Artificial
<220> FEATURE:
<223> OTHER INFORMATION: probe(2) for detecting human KIAA1199

<400> SEQUENCE: 15
atgacggtga ctcttggcag cagaccagtg ggggatggct gggtccccca gcccctgcca     60
gcagctgcct gggaaggccg tgtttcagcc ctgatgggcc aagggaaggc tatcagagac    120
cctggtgctg ccacctgccc ctactcaagt gtctacctgg agcccctggg gcggtgctgg    180
ccaatgctgg aaacattcac tttcctgcag cctcttgggt gcttctctcc tatctgtgcc    240
tcttcagtgg gggtttgggg accatatcag gagacctggg ttgtgctgac agcaaagatc    300
cactttggca ggagccctga cccagctagg aggtagtctg gagggctggt cattcacaga    360
tccccatggt cttcagcaga caagtgaggg tgg                                 393

<210> SEQ ID NO 16
<211> LENGTH: 624
<212> TYPE: DNA
<213> ORGANISM: Artificial
<220> FEATURE:
<223> OTHER INFORMATION: probe(3) for detecting human KIAA1199

<400> SEQUENCE: 16
ttgctgccac accacattgc ctcaacaacc ggccccagag tgcccaggca ctcctgaggt     60
agcttctgga aatggggaca gtcccctcg aaggaaagga aatgactaga gtagaatgac     120
```

```
agctagcaga tctcttccct cctgctccca gcgcacacaa acccgccctc cccttggtgt      180
tggcggtccc tgtggccttc actttgttca ctacctgtca gcccagcctg ggtgcacagt      240
agctgcaact ccccattggt gctacctggc tctcctgtct ctgcagctct acaggtgagg      300
cccagcagag ggagtagggc tcgccatgtt tctggtgagc caatttggct gatcttgggt      360
gtctgaacag ctattgggtc caccccagtc cctttcagct gctgcttaat gccctgctct      420
ctccctggcc caccttatag agagcccaaa gagctcctgt aagagggaga actctatctg      480
tggtttataa tcttgcacga ggcaccagag tctccctggg tcttgtgatg aactacattt      540 atccctttc ctgccccaac cacaaactct ttccttcaaa gagggcctgc ctggctccct      600
ccacccaact gcacccatga gact                                            624
```